United States Patent
Nii

(10) Patent No.: US 6,905,786 B2
(45) Date of Patent: Jun. 14, 2005

(54) LIGHT EMITTING DEVICE MATERIAL, LIGHT EMITTING DEVICE USING THEREOF, AND AMINE COMPOUND

(75) Inventor: Kazumi Nii, Kanagawa (JP)

(73) Assignee: Fuji Photo Film., Ltd., Kanagawa (JP)

( * ) Notice: Subject to any disclaimer, the term of this patent is extended or adjusted under 35 U.S.C. 154(b) by 127 days.

(21) Appl. No.: 10/308,037

(22) Filed: Dec. 3, 2002

(65) Prior Publication Data

US 2003/0138664 A1 Jul. 24, 2003

Related U.S. Application Data

(62) Division of application No. 09/664,407, filed on Sep. 18, 2000, now Pat. No. 6,514,633.

(30) Foreign Application Priority Data

Sep. 17, 1999 (JP) ........................................ P. 11-264380

(51) Int. Cl.⁷ .................. H05B 33/14; C09K 11/06; C07D 213/02; C07D 309/34; C07D 335/02
(52) U.S. Cl. ................ 428/690; 428/917; 313/504; 546/300; 546/304; 546/329; 549/13; 549/28; 549/416; 549/419; 549/424; 549/426
(58) Field of Search ................. 428/690, 917; 313/504; 252/301.16; 546/300, 304, 329; 549/13, 28, 416, 419, 424, 426

(56) References Cited

U.S. PATENT DOCUMENTS 6,451,456 B1 * 9/2002 Kim et al. .................. 428/690

FOREIGN PATENT DOCUMENTS

EP    0 866 110 A    9/1998
JP    7-133482 A    5/1995

* cited by examiner

*Primary Examiner*—Marie Yamnitzky
(74) *Attorney, Agent, or Firm*—Sughrue Mion, PLLC

(57) ABSTRACT

A compound represented by the following formula (I):

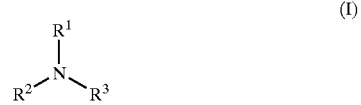

(I)

wherein $R^1$, $R^2$ and $R^3$ each represents an aryl group, a heterocyclic group or an aliphatic hydrocarbon group, provided that at least one of $R^1$, $R^2$ and $R^3$ represents an aryl group or a heterocyclic group and at least one of the aryl group and heterocyclic group contains a group represented by formula (II), $R^1$, $R^2$ and $R^3$ may be linked to each other to form a ring,

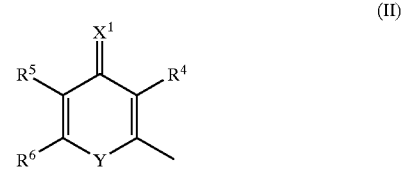

(II)

wherein $R^4$, $R^5$ and $R^6$, each represents a hydrogen atom or a substituent; $X^1$ represents an oxygen atom, a sulfur atom, N—$R^{X1}$ or $CR^{X2}R^{X3}$; $R^{X1}$, $R^{X2}$, $R^{X3}$ each represents a hydrogen atom or a substituent; $R^4$, $R^5$, $R^6$ and $X^1$ may be linked to each other to form a ring; Y represents an oxygen atom, a sulfur atom, or N—$R^{Y1}$; and $R^{Y1}$ represents a hydrogen atom or a substituent.

21 Claims, No Drawings

LIGHT EMITTING DEVICE MATERIAL, LIGHT EMITTING DEVICE USING THEREOF, AND AMINE COMPOUND

This is a divisional of application Ser. No. 09/664,407, filed Sep. 18, 2000, now U.S. Pat. No. 6,514,633; the disclosure of which is incorporated herein by reference.

FIELD OF THE INVENTION

The present invention relates to a compound suitable for use for a filter dye, a color conversion filter, a dye for a photographic material, a sensitizing dye, a dye for pulp-dyeing, a laser dye, a fluorescent medicine for a medical diagnosis, a material for a light emitting device (light emitting device material), etc., and particularly relates to a light emitting device using thereof.

BACKGROUND OF THE INVENTION

Prospects of the organic electroluminescence (EL) device in which organic materials are used are promising as a solid luminescent type inexpensive and large area full color display device and development has been tried variously. An organic light emitting device in general comprises a luminescent layer and a pair of counter electrodes with the luminescent layer between. When an electric field is impressed between both electrodes, electrons are injected from the cathode and positive holes are injected from the anode, and the electrons and the positive holes are recombined in the luminescent layer. A phenomenon of emitting energy as light when energy level is returned from conduction band to valence band is luminescence (light emitting).

Organic light emitting devices so far been used require high driving voltage and emission luminance and luminous efficacy are low, but an organic EL device (element) comprising lamination of thin layers containing an organic compound having high fluorescent quantum efficiency capable of emitting light with low voltage of 10 V or lower has been reported (*Applied Physics Letters*, Vol. 51, p. 913 (1987)) and attracting public attention in recent years. According to this technique, high luminance green light emission can be obtained by using a metal chelate complex as the electron-transporting layer, a fluorescent compound as the luminescent layer and an amine compound as the positive hole-transporting layer. Further, when taking into consideration the utilization of an organic light emitting device as a full color display and a light source, it is necessary to get three primary colors or a white color in practical use. A device capable of emitting a desired color by doping a fluorescent dye is reported (*Journal of Applied Physics*, Vol. 65, p. 3610 (1989)). This technique is particularly effective for red luminescence in which extinction due to concentration is large and the emission of high efficacy is difficult when a fluorescent dye is used alone as the luminescent layer, and high color purity and high luminance have been attained due to the technique. However, when a device doped with a dye is produced by deposition, the operation is complicated and the performance of the device is liable to become uneven because a host material and a trace amount of a fluorescent dye are co-deposited. Therefore, from the viewpoint of the simplification of the producing step and the stability of the performance of a device, the development of light emitting materials having good color purity and capable of using a dye alone as the luminescent layer, in particular, light emitting materials of from red to green capable of attaining good chromaticity and luminance and excellent in durability even when a dye is used alone as the luminescent layer has so far been desired.

On the other hand, organic EL devices which have realized high luminance emission are laminated devices formed by vacuum deposition of organic materials, but from the viewpoint of simplification of producing step, processability, and realization of large area devices, it is desired to produce devices by a coating system. However, devices produced by a coating system so far been used are inferior to devices produced by a deposition system in the points of emission luminance and luminous efficacy, therefore, the realizations of high luminance and high efficacy light emitting have been left as the problems to be solved. In addition, with devices produced by coating an organic low molecular weight compound dispersed in an organic polymer medium, uniform planar emission for a long period of time is difficult due to the agglomeration of the organic low molecular weight compound.

Further, in recent years, various materials having fluorescence have been used for a filter dye, a color conversion filter, a dye for a photographic material, a sensitizing dye, a dye for pulp-dyeing, a laser dye, a fluorescent medicine for a medical diagnosis, a material for an organic light emitting device, etc., and demand for such materials has been increased. However, fluorescent dyes having high fluorescent strength and high color purity are less, therefore, the development of a novel material has been desired.

SUMMARY OF THE INVENTION

A first object of the present invention is to provide a material for an organic light emitting device of green to red emission capable of emitting light with high luminance (light emitting) and high efficacy, excellent in stability at repeated use, and capable of uniform and planar emission with low voltage driving, and an organic light emitting device using the same.

A second object of the present invention is to provide a light emitting device showing no unevenness among devices and stable in performance, and a material capable of producing the light emitting device of green to red emission.

A third object of the present invention is to provide a material for an organic light emitting device capable of emitting light with high luminance and high efficacy even when produced by coating system, and an organic light emitting device using the same.

A fourth object of the present invention is to provide a compound having fluorescence of from green to red with high fluorescent strength.

These objects of the present invention have been accomplished by the following means.

(1) A material for a light emitting device (light emitting device material) which is a compound represented by the following formula (I):

wherein $R^1$, $R^2$ and $R^3$, which may be the same or different, each represents an aryl group, a heterocyclic group or an aliphatic hydrocarbon group, provided that at least one of $R^1$, $R^2$ and $R^3$ represents an aryl group or a heterocyclic group, $R^1$, $R^2$ and $R^3$ may be linked to each other to form a ring, $R^1$, $R^2$ and $R^3$ each may have a substituent, and at least one of the aryl group or the heterocyclic group represented by $R^1$, $R^2$ or $R^3$ contains a group represented by the following formula (II):

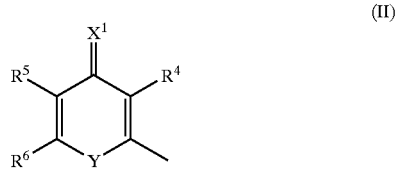

(II)

wherein $R^4$, $R^5$ and $R^6$, which may be the same or different, each represents a hydrogen atom or a substituent; $X^1$ represents an oxygen atom, a sulfur atom, N—$R^{X1}$ or $CR^{X2}R^{X3}$; $R^{X1}$, $R^{X2}$, $R^{X3}$, which may be the same or different, each represents a hydrogen atom or a substituent; $R^4$, $R^5$, $R^6$ and $X^1$ may be linked to each other to form a ring; Y represents an oxygen atom, a sulfur atom, or N—$R^{Y1}$; and $R^{Y1}$ represents a hydrogen atom or a substituent.

(2) The material for a light emitting device as described in the above item (1), wherein the compound represented by formula (I) is a compound represented by the following formula (III):

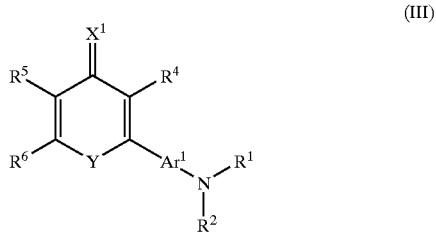

(III)

wherein $Ar^1$ represents a divalent aryl or heterocyclic group; $R^1$ and $R^2$, which may be the same or different, each represents an aryl group, a heterocyclic group or an aliphatic hydrocarbon group, $Ar^1$, $R^1$ and $R^2$ may be linked to each other to form a ring; $R^4$, $R^5$ and $R^6$, which may be the same or different, each represents a hydrogen atom or a substituent; $X^1$ represents an oxygen atom, a sulfur atom, N—$R^{X1}$ or $CR^{X2}R^{X3}$; $R^{X1}$, $R^{X2}$, $R^{X3}$, which may be the same or different, each represents a hydrogen atom or a substituent; $R^4$, $R^5$, $R^6$ and $X^1$ may be linked to each other to form a ring; Y represents an oxygen atom, a sulfur atom, or N—$R^{Y1}$; and $R^{Y1}$ represents a hydrogen atom or a substituent.

(3) The material for a light emitting device as described in the above item (1) or (2), wherein the compound represented by formula (III) is a compound represented by the following formula (IV):

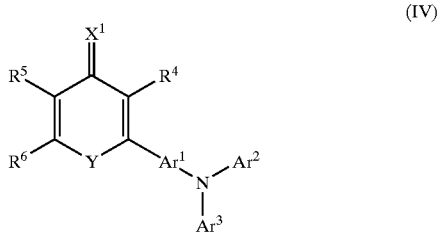

(IV)

wherein $Ar^1$ represents a divalent aryl or heterocyclic group; $Ar^2$ and $Ar^3$, which may be the same or different, each represents an aryl group or a heterocyclic group, $Ar^1$, $Ar^2$ and $Ar^3$ may be linked to each other to form a ring; $R^4$, $R^5$ and $R^6$, which may be the same or different, each represents a hydrogen atom or a substituent; $X^1$ represents an oxygen atom, a sulfur atom, N—$R^{X1}$ or $CR^{X2}R^{X3}$; $R^{X1}$, $R^{X2}$, $R^{X3}$, which may be the same or different, each represents a hydrogen atom or a substituent; $R^4$, $R^5$, $R^6$ and $X^1$ may be linked to each other to form a ring; Y represents an oxygen atom, a sulfur atom, or N—$R^{Y1}$; and $R^{Y1}$ represents a hydrogen atom or a substituent.

(4) An amine compound represented by the following formula (V):

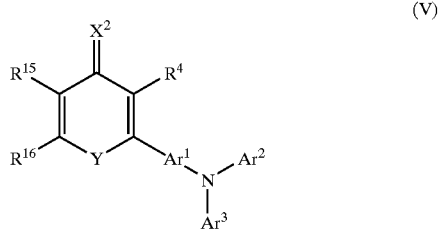

(V)

wherein $Ar^1$ represents a divalent aryl or heterocyclic group; $Ar^2$ and $Ar^3$, which may be the same or different, each represents an aryl group or a heterocyclic group, $Ar^1$, $Ar^2$ and $Ar^3$ may be linked to each other to form a ring; $R^4$, $R^{15}$ and $R^{16}$, which may be the same or different, each represents a hydrogen atom or a substituent; $X^2$ represents an oxygen atom, a sulfur atom, N—$R^{X4}$ or $CR^{X5}R^{X6}$; $R^{X4}$ represents a hydrogen atom, an aliphatic hydrocarbon group, an aryl group or a heterocyclic group, $R^{X5}$ and $R^{X6}$, which may be the same or different, each represents a hydrogen atom, an alkyl group, an aryl group, a heterocyclic group, a cyano group, an oxycarbonyl group, a carbamoyl group, a sulfonyl group, a sulfamoyl group, or an acyl group, provided that $R^{X5}$ and $R^{X6}$ do not represent hydrogen atoms at the same time, $R^{X5}$ and $R^{X6}$ may be linked to each other to form a ring; $R^4$, $R^{15}$, $R^{16}$ and $X^2$ may be linked to each other to form a ring, provided that $R^{15}$ and $R^{16}$ are not linked; Y represents an oxygen atom, a sulfur atom, or N—$R^{Y1}$; and $R^{Y1}$ represents a hydrogen atom or a substituent.

(5) An amine compound represented by the following formula (VI):

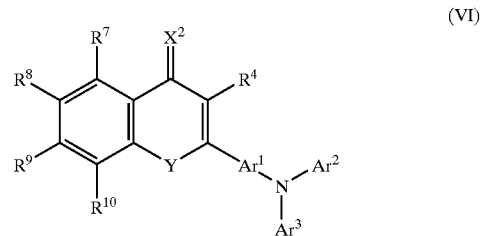

(VI)

wherein $Ar^1$ represents a divalent aryl or heterocyclic group; $Ar^2$ and $Ar^3$, which may be the same or different, each represents an aryl group or a heterocyclic group, $R^4$, $R^7$, $R^8$, $R^9$ and $R^{10}$, which may be the same or different, each represents a hydrogen atom or a substituent; $X^2$ represents an oxygen atom, a sulfur atom, N—$R^{X4}$ or $CR^{X5}R^{X6}$; $R^{X4}$ represents a hydrogen atom, an aliphatic hydrocarbon group, an aryl group or a heterocyclic group, $R^{X5}$ and $R^{X6}$, which may be the same or different, each represents a hydrogen atom, an alkyl group, an aryl group, a heterocyclic group, a cyano group, an oxycarbonyl group, a carbamoyl group, a sulfonyl group, a sulfamoyl group, or an acyl group, provided that $R^{X5}$ and $R^{X6}$ do not represent hydrogen atoms at the same time, and $R^{X5}$ and $R^{X6}$ may be linked to each other to form a ring; $R^4$, $R^7$, $R^8$, $R^9$, $R^{10}$ and $X^2$ may be linked to each other to form a ring; Y represents an oxygen atom, a sulfur atom, or N—$R^{Y1}$; and $R^{Y1}$ represents a hydrogen atom or a substituent, provided that when $X^2$ and Y both represent oxygen atoms and $Ar^1$ represents a phenyl group, at least one of $Ar^2$ and $Ar^3$ represents a substituted phenyl group, a naphthyl group or a heterocyclic group.

(6) A light emitting device comprising a pair of electrodes having formed therebetween at least one organic thin layer, wherein the organic thin layer contains at least one compound represented by formula (I) as described in the above item (1) or one compound represented by formula (III), (IV), (V) or (VI) as described in the above item (2), (3), (4) or (5).

(7) A light emitting device comprising a pair of electrodes having formed therebetween at least one organic thin layer, wherein at least one layer is a layer containing at least one compound represented by formula (I) as described in the above item (1) or one compound represented by formula (III), (IV), (V) or (VI) as described in the above item (2), (3), (4) or (5) dispersed in a polymer.

DETAILED DESCRIPTION OF THE INVENTION

In the first place, a compound represented by formula (I) will be described in detail below.

In formula (I), $R^1$, $R^2$ and $R^3$, which may be the same or different, each represents an aryl group, a heterocyclic group or an aliphatic hydrocarbon group, and at least one of $R^1$, $R^2$ and $R^3$ represents an aryl group or a heterocyclic group.

The aryl group represented by $R^1$, $R^2$ and $R^3$ includes a substituted aryl group and an unsubstituted aryl group. The aryl group represented by $R^1$, $R^2$ and $R^3$ may have a monocyclic structure or a polycyclic structure in which two or more rings are condensed. Examples of the aryl group represented by $R^1$, $R^2$ and $R^3$ include a monocylic to pentacylic aryl group having 6 to 30 carbon atoms (e.g., a phenyl group, a naphthyl group, an anthryl group, a phenanthryl group, a pyrenyl group, an indenyl group, a perylenyl group), preferably a phenyl, naphthyl, anthryl or phenanthryl group having 6 to 20 carbon atoms, more preferably a phenyl, naphthyl, anthryl or phenanthryl group having 6 to 14 carbon atoms.

The heterocyclic group represented by $R^1$, $R^2$ and $R^3$ is a 3- to 10-membered saturated or unsaturated heterocyclic ring containing at least one N, O or S atom. The heterocyclic ring may be a monocyclic ring or may form a condensed ring with other rings.

The heterocyclic group is preferably a 5- or 6-membered aromatic heterocyclic group, more preferably a 5- or 6-membered aromatic heterocyclic group containing a nitrogen atom, an oxygen atom or a sulfur atom, and still more preferably a 5- or 6-membered aromatic heterocyclic group containing one or two of a nitrogen atom or a sulfur atom. Specific examples of the heterocyclic rings include, e.g., pyrrolidine, piperidine, piperazine, morpholine, thiophene, furan, pyrrole, imidazole, pyrazole, pyridine, pyrazine, pyridazine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phenazine, tetrazole, benzimidazole, benzoxazole, benzothiazole, benzotriazole, and tetraazaindene, preferred examples include thiophene, pyridine and quinoline.

The aliphatic hydrocarbon group represented by $R^1$, $R^2$ and $R^3$ may be straight chain, branched or cyclic, and represents an alkyl group (preferably an alkyl group having from 1 to 20, more preferably from 1 to 12, and particularly preferably from 1 to 8, carbon atoms, e.g., methyl, ethyl, isopropyl, tert-butyl, n-octyl, n-decyl, n-hexadecyl, cyclopropyl, cyclopentyl, cyclohexyl), an alkenyl group (preferably an alkenyl group having from 2 to 20, more preferably from 2 to 12, and particularly preferably from 2 to 8, carbon atoms, e.g., vinyl, allyl, 2-butenyl, 3-pentenyl), or an alkynyl group (preferably an alkynyl group having from 2 to 20, more preferably from 2 to 12, and particularly preferably from 2 to 8, carbon atoms, e.g., propargyl, 3-pentynyl). The aliphatic hydrocarbon group is preferably an alkyl group.

The aryl group, heterocyclic group and aliphatic hydrocarbon group represented by $R^1$, $R^2$ and $R^3$ may have substituents, and examples of the substituents include, for example, an alkyl group (preferably an alkyl group having from 1 to 20, more preferably from 1 to 12, and particularly preferably from 1 to 8, carbon atoms, e.g., methyl, ethyl, isopropyl, tert-butyl, n-octyl, n-decyl, n-hexadecyl, cyclopropyl, cyclopentyl, cyclohexyl), an alkenyl group (preferably an alkenyl group having from 2 to 20, more preferably from 2 to 12, and particularly preferably from 2 to 8, carbon atoms, e.g., vinyl, allyl, 2-butenyl, 3-pentenyl), an alkynyl group (preferably an alkynyl group having from 2 to 20, more preferably from 2 to 12, and particularly preferably from 2 to 8, carbon atoms, e.g., propargyl, 3-pentynyl), an aryl group (preferably an aryl group having from 6 to 30, more preferably from 6 to 20, and particularly preferably from 6 to 12, carbon atoms, e.g., phenyl, p-methylphenyl, naphthyl), an amino group (preferably an amino group having from 0 to 20, more preferably from 0 to 12, and particularly preferably from 0 to 6, carbon atoms, e.g., amino, methylamino, dimethylamino, diethylamino, dibenzylamino), an alkoxyl group (preferably an alkoxyl group having from 1 to 20, more preferably from 1 to 12, and particularly preferably from 1 to 8, carbon atoms, e.g., methoxy, ethoxy, butoxy), an aryloxy group (preferably an aryloxy group having from 6 to 20, more preferably from 6 to 16, and particularly preferably from 6 to 12, carbon atoms, e.g., phenyloxy, 2-naphthyloxy), an acyl group (preferably an acyl group having from 1 to 20, more preferably from 1 to 16, and particularly preferably from 1 to 12, carbon atoms, e.g., acetyl, benzoyl, formyl, pivaloyl), an alkoxycarbonyl group (preferably an alkoxycarbonyl group having from 2 to 20, more preferably from 2 to 16, and particularly preferably from 2 to 12, carbon atoms, e.g., methoxycarbonyl, ethoxycarbonyl), an aryloxycarbonyl group (preferably an aryloxycarbonyl group having from 7 to 20, more preferably from 7 to 16, and particularly preferably from 7 to 10, carbon atoms, e.g., phenyloxycarbonyl), an acyloxy group (preferably an acyloxy group having from 2 to 20, more preferably from 2 to 16, and particularly preferably from 2 to 10, carbon atoms, e.g., acetoxy, benzoyloxy), an acylamino group (preferably an acylamino group having from 2 to 20, more preferably from 2 to 16, and particularly preferably from 2 to 10, carbon atoms, e.g., acetylamino, benzoylamino), an alkoxycarbonylamino group (preferably an alkoxycarbonylamino group having from 2 to 20, more preferably from 2 to 16, and particularly preferably from 2 to 12, carbon atoms, e.g., methoxycarbonylamino), an aryloxycarbonylamino group (preferably an aryloxycarbonylamino group having from 7 to 20, more preferably from 7 to 16, and particularly preferably from 7 to 12, carbon atoms, e.g., phenyloxycarbonylamino), a sulfonylamino group (preferably a sulfonylamino group having from 1 to 20, more preferably from 1 to 16, and particularly preferably from 1 to 12, carbon atoms, e.g., methanesulfonylamino, benzenesulfonylamino), a sulfamoyl group (preferably a sulfamoyl group having from 0 to 20, more preferably from 0 to 16, and particularly preferably from 0 to 12, carbon atoms, e.g., sulfamoyl, methylsulfamoyl, dimethylsulfamoyl, phenyl-sulfamoyl), a carbamoyl group (preferably a carbamoyl group having from 1 to 20, more preferably from 1 to 16, and particularly preferably from 1 to 12, carbon atoms, e.g., carbamoyl, methylcarbamoyl, diethylcarbamoyl, phenylcarbamoyl), an alkylthio group (preferably an alkylthio group having from 1 to 20, more preferably from 1 to 16, and particularly preferably from 1 to 12, carbon atoms, e.g., methylthio, ethylthio), an arylthio group (preferably an arylthio group having from 6 to 20, more preferably from 6 to 16, and particularly preferably from 6 to 12, carbon atoms, e.g., phenylthio), a sulfonyl group (preferably a sulfonyl group having from 1 to 20, more preferably from 1 to 16, and particularly preferably from 1 to 12, carbon atoms, e.g., mesyl, tosyl), a sulfinyl group (preferably a sulfinyl group having from 1 to 20, more preferably from 1 to 16, and particularly preferably from 1 to 12, carbon atoms, e.g., methanesulfinyl, benzenesulfinyl), a ureido group (preferably a ureido group having from 1 to 20, more preferably from 1 to 16, and particularly preferably from 1 to 12, carbon atoms, e g., ureido, methylureido, phenylureido), a phosphoric acid amido group (preferably a phosphoric acid amido group having from 1 to 20, more preferably from 1 to 16, and particularly preferably from 1 to 12, carbon atoms, e.g., diethylphosphoricacidamido, phenylphosphoricacid amido), a hydroxyl group, a mercapto group, a halogen atom (e.g., fluorine, chlorine, bromine, iodine), acyanogroup, asulfogroup, a carboxyl group, a nitro group, a hydroxamic acid group, a sulfino group, a hydrazino group, an imino group, a heterocyclic group (preferably a heterocyclic group having from 1 to 20, and more preferably from 1 to 12, carbon atoms; as hetero atoms, e.g., nitrogen, oxygen, sulfur, and specifically, e.g., pyrrolidine, piperidine, piperazine, morpholine, thiophene, furan, pyrrole, imidazole, pyrazole, pyridine, pyrazine, pyridazine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phenazine, tetrazole, benzimidazole, benzoxazole, benzothiazole, benzotriazole, and tetraazaindene can be exemplified), and a silyl group (preferably a silyl group having from 3 to 40, more preferably from 3 to 30, and particularly preferably from 3 to 24, carbon atoms, e.g., trimethylsilyl, triphenylsilyl). These substituents may further be substituted. When there are two or more substituents, they may be the same or different. Substituents may be linked to each other to form a ring, if possible.

Preferred examples of the substituents include an alkyl group, an alkenyl group, an aralkyl group, an aryl group, an alkoxyl group, an amino group, an acyl group, an alkoxycarbonyl group, an aryloxycarbonyl group, a carbonylamino group, a sulfonylamino group, a sulfamoyl group, a carbamoyl group, a hydroxyl group, and a heterocyclic group, more preferred examples include an alkyl group, an alkenyl group, an aralkyl group, an aryl group, an alkoxyl group, an amino group, a carbonylamino group, a sulfonylamino group, and a heterocyclic group, and still more preferred examples include an alkyl group, an alkenyl group, an aryl group, an alkoxyl group, and a substituted amino group.

Here, the substituted amino group is a group represented by —NRa(Rb), wherein Ra and Rb may be the same or different, and specifically represents an alkyl group, an alkenyl group, an aralkyl group, an aryl group, or a heterocyclic group.

$R^1$, $R^2$ and $R^3$ may be linked to each other to form a ring, preferably 5- to 7-membered rings.

At least one of $R^1$, $R^2$ or $R^3$ contains a group represented by the following formula (II):

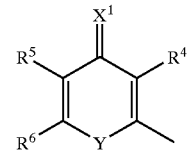

(II)

wherein $R^4$, $R^5$ and $R^6$ each represents a hydrogen atom or a substituent, and examples of the substituents are the same as those defined above as the substituents of $R^1$, $R^2$ and $R^3$; $R^4$, $R^5$, $R^6$ and $X^1$ may be linked to form a ring, preferably $R^5$ and $R^6$ are linked to each other to form a ring, and the ring formed by linking preferably represents an aromatic carbocyclic ring or an aromatic heterocyclic ring.

$X^1$ represents an oxygen atom, a sulfur atom, N—$R^{X1}$ or $CR^{X2}R^{X3}$. $X^1$ preferably represents an oxygen atom, a sulfur atom or $CR^{X2}R^{X3}$, and $R^{X1}$, $R^{X2}$ and $R^{X3}$ each represents a hydrogen atom or a substituent, and examples of the substituents are the same as those defined above as the substituents of $R^1$, $R^2$ and $R^3$. $R^{X1}$ preferably represents a hydrogen atom, an alkyl group, an aryl group or a heterocyclic group, and $R^{X2}$ and $R^{X3}$ each preferably represents a hydrogen atom, an alkyl group, an aryl group, a heterocyclic group, a cyano group, an oxycarbonyl group, a carbamoyl group, a sulfonyl group, a sulfamoyl group or an acyl group. $R^{X2}$ and $R^{X3}$ do not represent hydrogen atoms at the same time. More preferably, $R^{X1}$ represents an alkyl group, an aryl group or a heterocyclic group, and these groups have the same meaning as defined above in the alkyl, aryl and heterocyclic groups represented by $R^1$, $R^2$ and $R^3$, and specific examples are also the same.

The alkyl group represented by $R^{X2}$ and $R^{X3}$ is preferably a perfluoroalkyl group, i.e., a straight chain, branched or cyclic alkyl group having a fluorine atom as a substituent (preferably an alkyl group having from 1 to 30, more preferably from 1 to 20, and still more preferably from 1 to 12, carbon atoms, e.g., trifluoromethyl, pentafluoromethyl).

The oxycarbonyl group, the carbamoyl group, the sulfonyl group, the sulfamoyl group or the acyl group represented by $R^{X2}$ and $R^{X3}$ is preferably an oxycarbonyl group, a carbamoyl group, a sulfonyl group, a sulfamoyl group or an acyl group substituted with an aliphatic hydrocarbon group, an aryl group or a heterocyclic group.

The aliphatic hydrocarbon group in this case has the same meaning as the aliphatic hydrocarbon group represented by $R^1$, $R^2$ and $R^3$, preferably an alkyl group or an alkenyl group, and more preferably a methyl group, an ethyl group, a propyl group, a butyl group, a trifluoromethyl group, or an allyl group.

The aryl group in this case preferably has the same meaning as the aryl group represented by $R^1$, $R^2$ and $R^3$. The heterocyclic group in this case preferably has the same meaning as the heterocyclic group represented by $R^1$, $R^2$ and $R^3$. These groups may be monocyclic or may form a condensed ring with other rings.

$R^{X2}$ and $R^{X3}$ may be linked to each other to form a ring. The ring formed by linking $R^{X2}$ and $R^{X3}$ is preferably represented by the following formula (A):

(A)

wherein $X^A$ represents an oxygen atom, a sulfur atom, N—$R^{A1}$ or $CR^{A2}R^{A3}$; $R^{A1}$, $R^{A2}$ and $R^{A3}$ each represents a hydrogen atom or a substituent; and $Z^A$ represents an atomic group to form a 5- to 7-membered ring, preferably an atomic group to form a 5- to 7-membered ring comprising any of a carbon atom, a nitrogen atom, an oxygen atom, and a sulfur atom.

The substituents represented by $R^{A1}$, $R^{A2}$ and $R^{A3}$ have the same meaning as the substituents represented by $R^1$, $R^2$ and $R^3$, respectively. $R^{A1}$ preferably represents a hydrogen atom, an aliphatic hydrocarbon group, an aryl group or a heterocyclic group.

The aliphatic hydrocarbon group represented by $R^{A1}$ is preferably a straight chain, branched or cyclic alkyl group (preferably an alkyl group having from 1 to 30, more preferably from 1 to 20, and still more preferably from 1 to 12, carbon atoms, e.g., methyl, ethyl, isopropyl, tert-butyl, n-octyl, n-decyl, n-hexadecyl, cyclopropyl, cyclopentyl, cyclohexyl), an alkenyl group (preferably an alkenyl group having from 2 to 30, more preferably from 2 to 20, and still more preferably from 2 to 12, carbon atoms, e.g., vinyl, allyl, 2-butenyl, 3-pentenyl), or an alkynyl group (preferably an alkynyl group having from 2 to 30, more preferably from 2 to 20, and still more preferably from 2 to 12, carbon atoms, e.g., propargyl, 3-pentynyl), more preferably an alkyl group or an alkenyl group, and still more preferably a methyl group, an ethyl group, a propyl group, a butyl group or an allyl group.

The aryl group represented by $R^{A1}$ is preferably a monocyclic or bicyclic aryl group having from 6 to 30 carbon atoms (e.g., phenyl, naphthyl), more preferably a phenyl group having from 6 to 20 carbon atoms, and still more preferably a phenyl group having from 6 to 12 carbon atoms.

The heterocyclic group represented by $R^{A1}$ is preferably a 3- to 10-membered saturated or unsaturated heterocyclic ring containing at least one N, O or S atom. The heterocyclic ring may be a monocyclic ring or may form a condensed ring with other rings.

The heterocyclic group is preferably a 5- or 6-membered aromatic heterocyclic group, more preferably a 5- or 6-membered aromatic heterocyclic group containing a nitrogen atom, and still more preferably a 5- or 6-membered aromatic heterocyclic group containing one or two nitrogen atom(s). Specific examples of the heterocyclic rings include, e.g., pyrrolidine, piperidine, piperazine, morpholine, thiophene, furan, pyrrole, imidazole, pyrazole, pyridine, pyrazine, pyridazine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phenazine, tetrazole, benzimidazole, benzoxazole, benzothiazole, benzotriazole, and tetraazaindene. Of these, preferred heterocyclic rings are pyrrole, imidazole, pyrazole, pyridine, pyrazine, pyridazine, triazole, triazine, indole, indazole, thiadiazole, oxadiazole, quinoline, phthalazine, quinoxaline, quinazoline, cinnoline, tetrazole, thiazole, oxazole, benzimidazole, benzoxazole, benzothiazole, and benzotriazole, and more preferred are imidazole, pyridine, quinoline, thiazole, oxazole, benzimidazole, benzoxazole, benzothiazole, and benzotriazole, and still more preferred are pyridine and quinoline.

The aliphatic hydrocarbon group, the aryl group or the heterocyclic group represented by $R^{A1}$ may have substituents, and the substituents defined above as the substituents of $R^1$, $R^2$ and $R^3$ can be exemplified as the substituents thereof.

$R^{A1}$ preferably represents an alkyl group, an alkenyl group or an aryl group, more preferably an alkyl group or a phenyl group.

$R^{A2}$ and $R^{A3}$ each preferably represents a hydrogen atom, a cyano group, an oxycarbonyl group, an acyl group, a sulfonyl group, a thioether group, a carbamoyl group or a sulfamoyl group (provided that $R^{A2}$ and $R^{A3}$ do not represent hydrogen atoms at the same time).

The oxycarbonyl group, the acyl group, the sulfonyl group or the thioether group represented by $R^{A2}$ and $R^{A3}$ is an oxycarbonyl group, an acyl group, a sulfonyl group or a thioether group substituted with an aliphatic hydrocarbon group, an aryl group or a heterocyclic group. In this case, the aliphatic hydrocarbon group, the aryl group and the heterocyclic group moieties have the same meaning as the aliphatic hydrocarbon group, the aryl group and the heterocyclic group represented by $R^1$ described above.

The carbamoyl group or the sulfamoyl group represented by $R^{A2}$ and $R^{A3}$ is an unsubstituted carbamoyl group or sulfamoyl group or substituted with an aliphatic hydrocarbon group, an aryl group or a heterocyclic group. In this case, the aliphatic hydrocarbon group, the aryl group and the heterocyclic group moieties have the same meaning as the aliphatic hydrocarbon group, the aryl group and the heterocyclic group represented by $R^{A1}$ described above.

The compound represented by formula (A) is preferably represented by the following formula (B), (C), (D), (E), (F) or (G).

The compound represented by formula (B) will be described below.

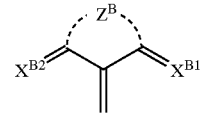

(B)

wherein $X^{B1}$ and $X^{2B}$ each represents an oxygen atom, a sulfur atom, N—$R^{B1}$ or $CR^{B2}$ $R^{B3}$; $R^{B1}$, $R^{B2}$ and $R^{B3}$ each represents a hydrogen atom or a substituent; and $Z^B$ represents an atomic group to form a 5- to 7-membered ring, preferably an atomic group to form a 5- to 7-membered ring comprising any of a carbon atom, a nitrogen atom, an oxygen atom, and a sulfur atom. The 5- to 7-membered ring formed by $Z^B$ may further form a condensed ring. $R^{B1}$, $R^{B2}$ and $R^{B3}$ have the same meaning as $R^{A1}$, $R^{A2}$ and $R^{A3}$ described above.

Specific examples of the compounds represented by formula (B) include, e.g., a 1,3-indanedione nucleus, a 3,5-pyrazolinedione nucleus, a 1,3-cyclohexanedione nucleus, a 1,3-dioxane-4,6-dione nucleus, and a 2,4,6-triketohexahydro-pyrimidine nucleus (e.g., barbituric acid or 2-thiobarbituric acid and derivatives thereof, and as derivatives, e.g., 1-alkyl form such as 1-methyl, 1-ethyl; 1,3-dialkyl form such as 1,3-dimethyl, 1,3-diethyl, 1,3-dibutyl; 1,3-diaryl form such as 1,3-diphenyl, 1,3-di(p-chlorophenyl), 1,3-di(p-ethoxycarbonylphenyl); 1-alkyl-1-aryl form such as 1-ethyl-3-phenyl; and 1,3-di-heterocyclic ring substitution form such as 1,3-di(2-pyridyl). More specifically, the following compounds and the derivatives thereof can be exemplified.

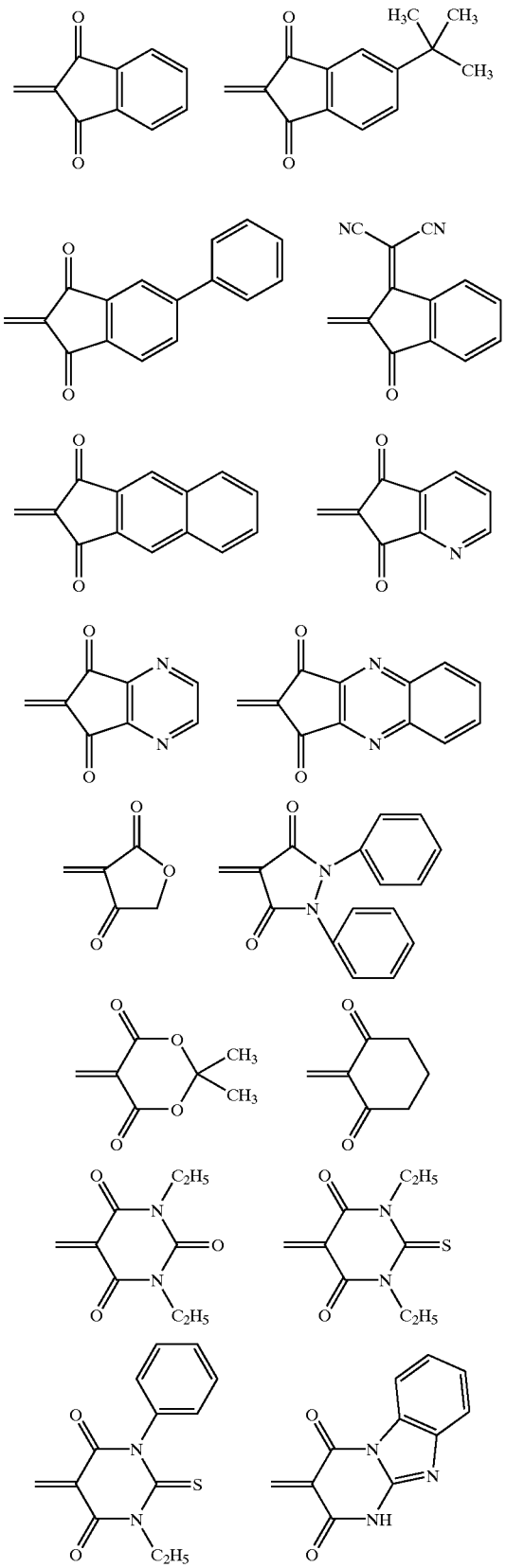
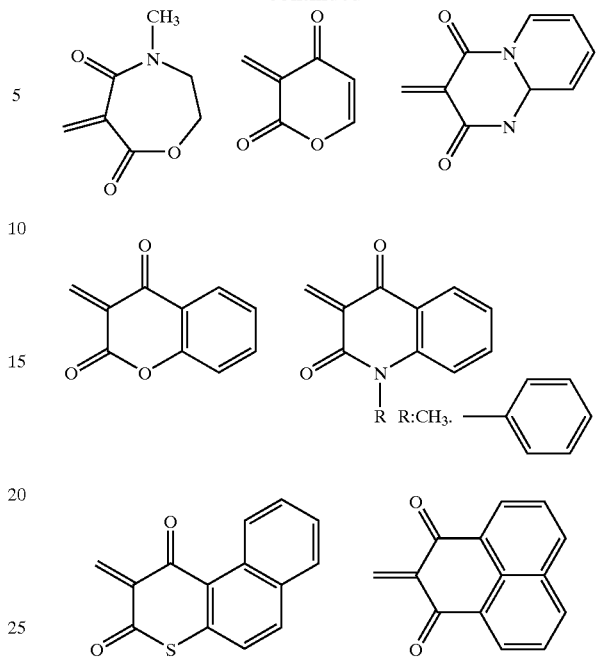

The compound represented by formula (C) will be described below.

$$\text{(C)}$$

wherein $X^C$ represents an oxygen atom, a sulfur atom, $N-R^{C1}$ or $CR^{C2}R^{C3}$; $R^{C1}$, $R^{C2}$ and $R^{C3}$ each represents a hydrogen atom or a substituent; $Y^{C1}$ and $Y^{C2}$ each represents a nitrogen atom or $C-R^{C4}$; $R^{C4}$ represents a hydrogen atom or a substituent, and the substituents exemplified as the substituents of $R^1$, $R^2$ and $R^3$ can be applied thereto; and $Z^C$ represents an atomic group to form a 5- to 7-membered ring, preferably an atomic group to form a 5- to 7-membered ring comprising any of a carbon atom, a nitrogen atom, an oxygen atom, and a sulfur atom. The 5- to 7-membered ring formed by $Z^C$ may further form a condensed ring. $R^{C1}$, $R^{C2}$ and $R^{C3}$ have the same meaning as $R^{A1}$, $R^{A2}$ and $R^{A3}$ described above.

Specific examples of the compounds represented by formula (C) include, e.g., a pyrazolone nucleus, an isooxazolinone nucleus, an oxazolinone nucleus, a furanone nucleus, an oxyindole nucleus, an imidazolidone nucleus and a 1,2,3,6-tetrahydropyridine-2,6-dione nucleus. More specifically, the following compounds and the derivatives thereof can be exemplified.

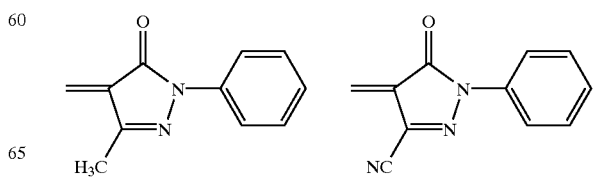

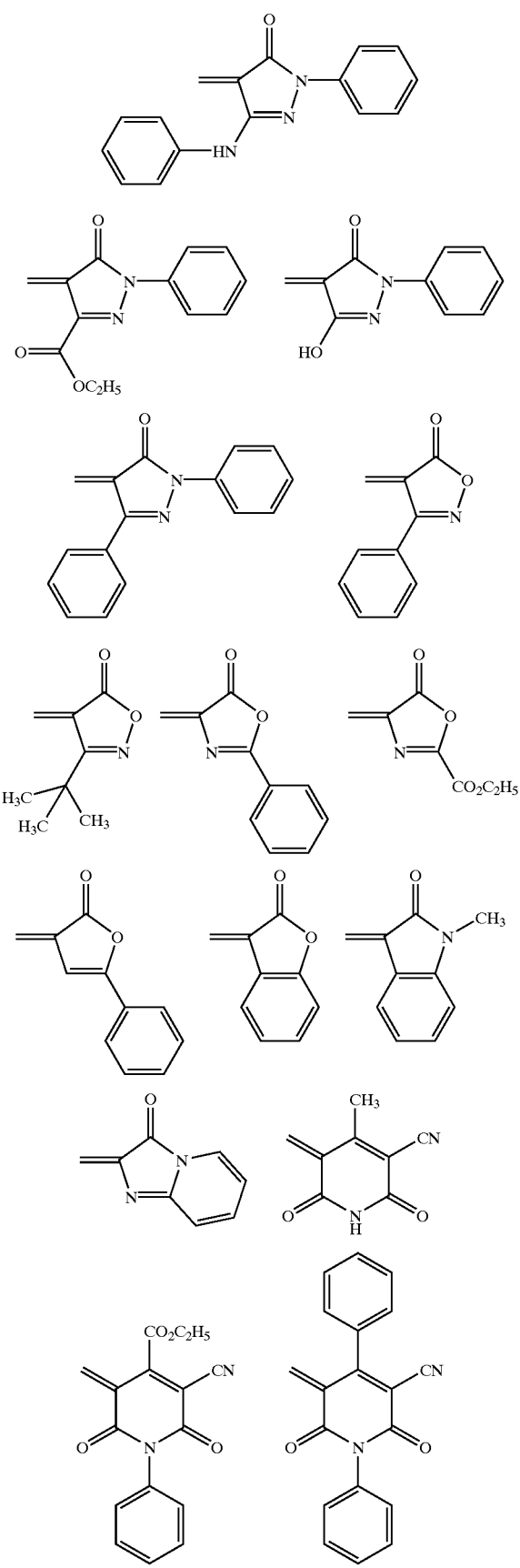
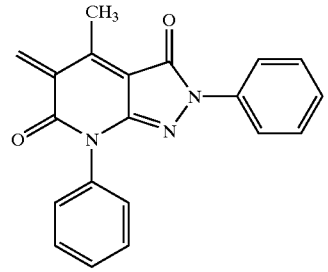

The compound represented by formula (D) will be described below.

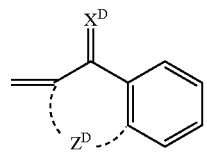

wherein $X^D$ represents an oxygen atom, a sulfur atom, $N-R^{D1}$ or $CR^{D2}R^{D3}$; $R^{D1}$, $R^{D2}$ and $R^{D3}$ each represents a hydrogen atom or a substituent; and $Z^D$ represents an atomic group to form a 5- to 7-membered ring, preferably an atomic group to form a 5- to 7-membered ring comprising any of a carbon atom, a nitrogen atom, an oxygen atom, and a sulfur atom. $R^{D1}$, $R^{D2}$ and $R^{D3}$ have the same meaning as $R^{A1}$, $R^{A2}$ and $R^{A3}$ described above.

As the specific examples of the compounds represented by formula (D), the following compounds and the derivatives thereof can be exemplified.

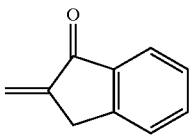 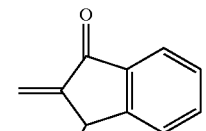
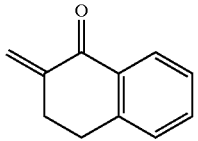 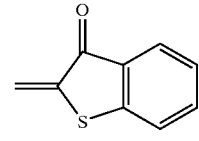
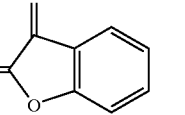 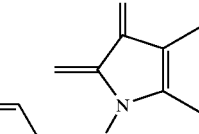
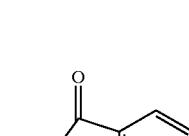 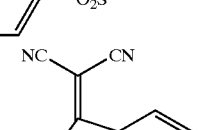
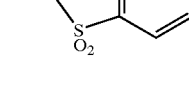 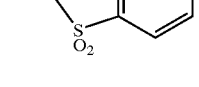

The compound represented by formula (E) will be described below.

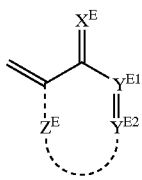

(E)

wherein $X^E$ represents an oxygen atom, a sulfur atom, N—$R^{E1}$ or $CR^{E2}R^{E3}$; $R^{E1}$, $R^{E2}$ and $R^{E3}$ each represents a hydrogen atom or a substituent; $Y^{E1}$ and $Y^{E2}$ each represents a nitrogen atom or C—$R^{E4}$; $R^{E4}$ represents a hydrogen atom or a substituent, and the substituents exemplified as the substituents of $R^1$, $R^2$ and $R^3$ can be applied thereto; and $Z^E$ represents an atomic group to form a 5- to 7-membered ring, preferably an atomic group to form a 5- to 7-membered ring comprising any of a carbon atom, a nitrogen atom, an oxygen atom, and a sulfur atom. The 5- to 7-membered ring formed by $Z^E$ may further form a condensed ring. $R^{E1}$, $R^{E2}$ and $R^{E3}$ have the same meaning as $R^{A1}$, $R^{A2}$ and $R^{A3}$ described above.

As the specific examples of the compounds represented by formula (E), the following compounds and the derivatives thereof can be exemplified.

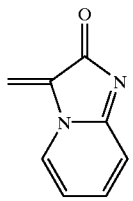
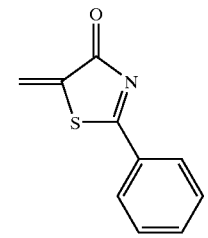
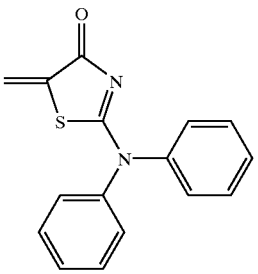

The compound represented by formula (F) will be described below.

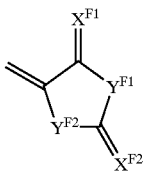

(F)

wherein $X^{F1}$ and $X^{F2}$ each represents an oxygen atom, a sulfur atom, N—$R^{F1}$ or $CR^{F2}R^{F3}$; $R^{F1}$, $R^{F2}$ and $R^{F3}$ each represents a hydrogen atom or a substituent; $Y^{F1}$ and $Y^{F2}$ each represents an oxygen atom, a sulfur atom or N—$R^{F5}$; $R^{F1}$ and $R^{F5}$ have the same meaning as $R^{A1}$ described above, and $R^{F2}$ and $R^{F3}$ have the same meaning as $R^{A2}$ and $R^{A3}$ described above.

As the specific example of the acid nuclei represented by formula (F), e.g., a 2-thio-2,4-thiazolidinedione nucleus (e.g., rhodanine and derivatives thereof, and as derivatives, e.g., 3-alkylrhodanine such as 3-methylrhodanine, 3-ethylrhodanine, 3-allylrhodanine; 3-arylrhodanine such as 3-phenylrhodanine; and 3-heterocyclic ring substituted rhodanine such as 3-(2-pyridyl)rhodanine), a 2-thio-2,4-oxazolidinedione nucleus, a 2-thio-2,4-(3H,5H)-oxazoledione nucleus, a 2-thio-2,5-thiazolidinedione nucleus, a 2,4-thiazolidinedione nucleus, a thiazolin-4-one nucleus, a 4-thiazolidinone nucleus, a 2,4-imidazolidinedione (hydantoin) nucleus, a 2-thio-2,4-imidazolidinedione (2-thiohydantoin) nucleus, an imidazolin-5-one nucleus, and analogs thereof can be exemplified.

More specifically, the following compounds can be exemplified.

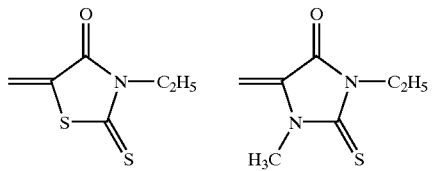

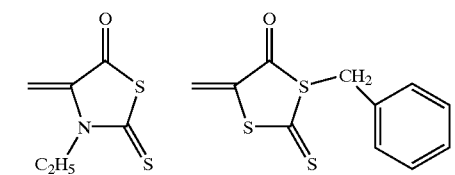

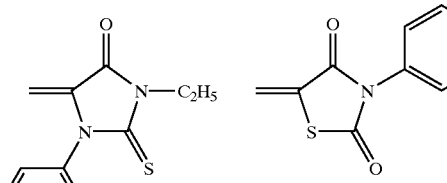

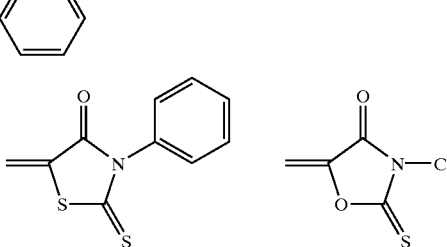

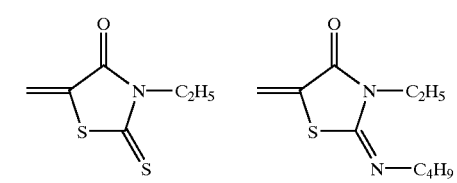

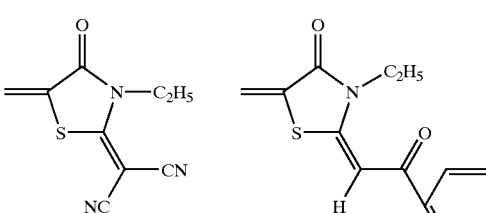

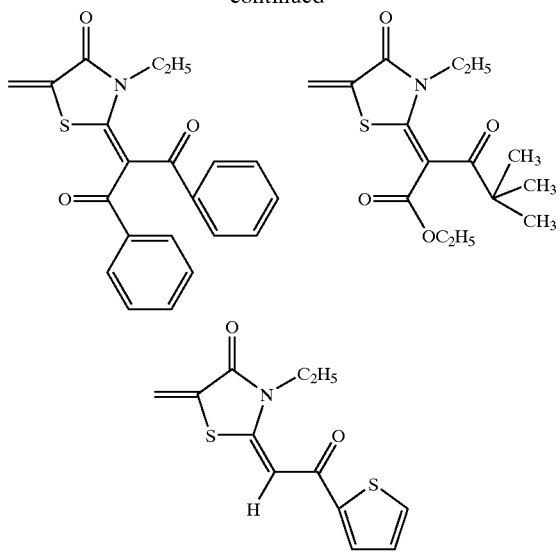

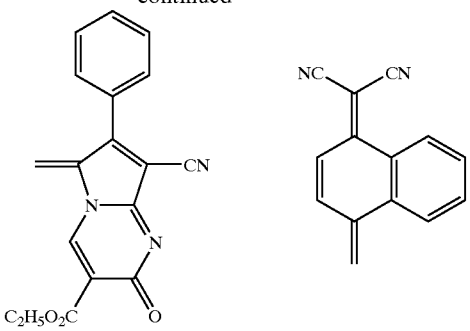

The compound represented by formula (G) will be described below.

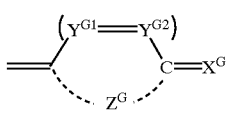

wherein $X^G$ represents an oxygen atom, a sulfur atom, $N\text{—}R^{G1}$ or $CR^{G2}R^{G3}$; $R^{G1}$, $R^{G2}$ and $R^{G3}$ each represents a hydrogen atom or a substituent; $Y^{G1}$ and $Y^{G2}$ each represents a nitrogen atom or $C\text{—}R^{G4}$; $R^{G4}$ represents a hydrogen atom or a substituent, and the substituents exemplified as the substituents of $R^1$, $R^2$ and $R^3$ can be applied thereto; m1 represents 1 or 2; and $Z^G$ represents an atomic group to form a 5- to 7-membered ring, preferably an atomic group to form a 5- to 7-membered ring comprising any of a carbon atom, a nitrogen atom, an oxygen atom, and a sulfur atom. The 5- to 7-membered ring formed by $Z^G$ may further form a condensed ring. $R^{G1}$, $R^{G2}$ and $R^{G3}$ have the same meaning as $R^{A1}$, $R^{A2}$ and $R^{A3}$ described above.

As the specific examples of the compounds represented by formula (G), the following compounds can be exemplified.

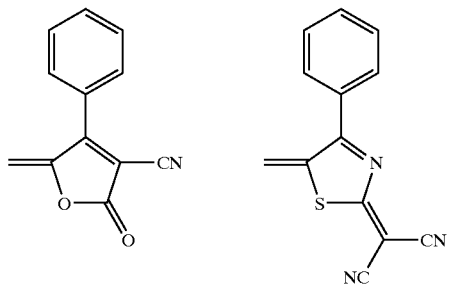

Further, $X^A$ in the above formula (A) may further be condensed with the acid nuclei represented by formula (A). For example, the following examples can be exemplified taking the rhodanine nucleus represented by formula (F) as an example.

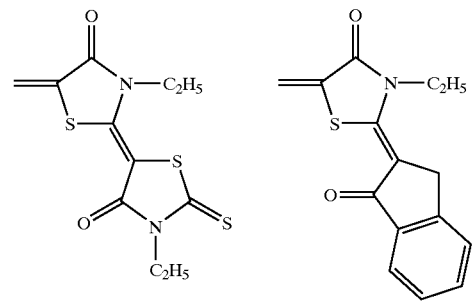

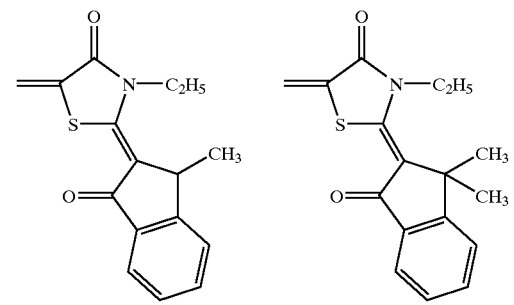

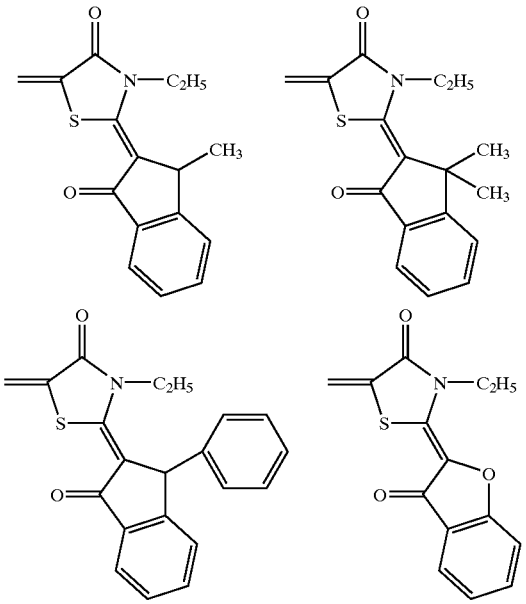

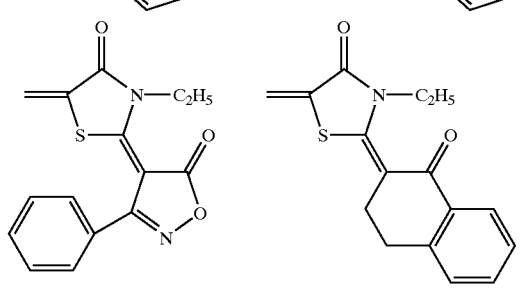

-continued

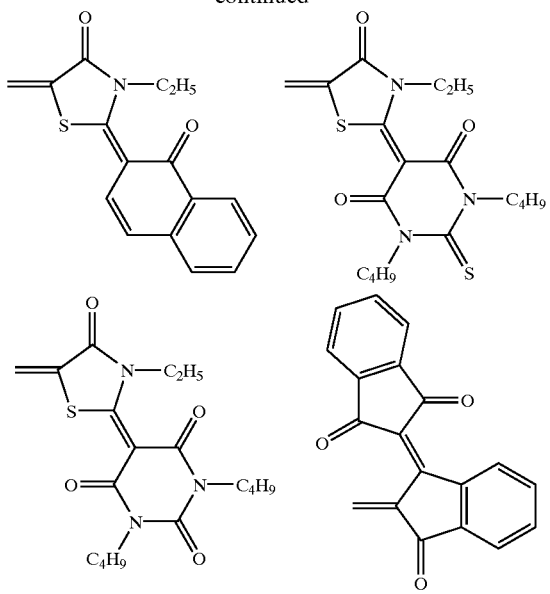

Preferred examples of the compounds represented by formulae (A) to (G) are shown below, e.g., a 1,3-indanedione nucleus, a 3,5-pyrazolinedione nucleus, a 1,3-cyclohexanedione nucleus (including thioketone forms), a 1,3-dioxane-4,6-dione nucleus, a 2,4,6-triketohexahydropyrimidine nucleus (including thioketone forms), a pyrazolone nucleus, an isooxazolinone nucleus, an oxazolinone nucleus, a furanone nucleus, an oxyindole nucleus, an imidazolidone nucleus, a 1,2,3,6-tetrahydropyridine-2,6-dione nucleus, a benzothiophen-3-one nucleus, an oxobenzothiophen-3-one nucleus, a dioxobenzothiophen-3-one nucleus, a coumaranone nucleus, an oxyindole nucleus, a 1-indanone nucleus, an α-tetralone nucleus, a 2-thio-2,4-thiazolidinedione nucleus, a 2-thio-2,4-oxazolidinedione nucleus, a 2-thio-2,5-thiazolidinedione nucleus, a 2,4-thiazolidinedione nucleus, a 2,4-imidazolidinedione nucleus, a 2-thio-2,4-imidazolidinedione nucleus, and an 2-imidazolin-5-one nucleus, more preferred are a 1,3-indanedione nucleus, a 2,4,6-triketohexahydropyrimidine nucleus (including thioketone forms), a pyrazolone nucleus, an isooxazolinone nucleus, an oxazolinone nucleus, a furanone nucleus, an oxyindole nucleus, an imidazolidone nucleus, a 1,2,3,6-tetrahydropyridine-2,6-dione nucleus, a benzothiophen-3-one nucleus, an oxobenzothiophen-3-one nucleus, a dioxobenzothiophen-3-one nucleus, a coumaranone nucleus, an oxyindole nucleus, a 1-indanone nucleus, a 2-thio-2,4-thiazolidinedione nucleus, a 2-thio-2,4-oxazolidinedione nucleus, a 2-thio-2,5-thiazolidinedione nucleus, and a 2,4-thiazolidinedione nucleus, and particularly preferred are a 1,3-indanedione nucleus, a barbituric acid derivative, a 2-thiobarbituric acid derivative, a pyrazolone nucleus, an isooxazolinone nucleus, an oxazolinone nucleus, a furanone nucleus, an imidazolidone nucleus, a 1,2,3,6-tetrahydropyridine-2,6-dione nucleus, an oxobenzothiophen-3-one nucleus, a dioxobenzothiophen-3-one derivative, a 2-thio-2,4-thiazolidinedione nucleus, a 1-indanone nucleus and a 2-thio-2,4-oxazolidinedione nucleus.

For producing a device showing good red color purity, $X^1$ preferably represents $CR^{X2}R^{X3}$.

Y represents an oxygen atom, a sulfur atom, or N—$R^{Y1}$; and $R^{Y1}$ represents a hydrogen atom or a substituent. $R^{Y1}$ has the same meaning as $R^{X1}$. Y preferably represents an oxygen atom, a sulfur atom, or N—$R^{Y1}$ (provided that $R^{Y1}$ represents an alkyl group). Y particularly preferably represents an oxygen atom or a sulfur atom, and most preferably represents an oxygen atom.

The compound represented by formula (III) will be described below.

In formula (III), $Ar^1$ represents a divalent aryl or heterocyclic group. The divalent aryl group represented by $Ar^1$ is preferably a monocyclic or bicyclic aryl group having from 6 to 30 carbon atoms (e.g., phenyl, naphthyl), more preferably a phenyl or naphthyl group having from 6 to 20 carbon atoms, and still more preferably a phenyl or naphthyl group having from 6 to 14 carbon atoms.

The divalent heterocyclic group represented by $Ar^1$ is a 3- to 10-membered saturated or unsaturated heterocyclic ring containing at least one N, O or S atom. The heterocyclic ring may be a monocyclic ring or may further form a condensed ring with other rings.

The heterocyclic group is preferably a 5- or 6-membered aromatic heterocyclic group, more preferably a 5- or 6-membered aromatic heterocyclic group containing a nitrogen atom, an oxygen atom or a sulfur atom, and still more preferably a 5- or 6-membered aromatic heterocyclic group containing one or two of a nitrogen atom or a sulfur atom. Specific examples of the heterocyclic rings include, e.g., pyrrolidine, piperidine, piperazine, morpholine, thiophene, furan, pyrrole, imidazole, pyrazole, pyridine, pyrazine, pyridazine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phenazine, tetrazole, benzimidazole, benzoxazole, benzothiazole, benzotriazole, and tetraazaindene, preferred examples include thiophene, pyridine and quinoline.

$R^1$, $R^2$, $R^4$, $R^5$, $R^6$, $X^1$ and Y have the same meaning as those in formula (I) and the preferred ranges are also the same.

The compound represented by formula (IV) will be described below.

In formula (IV), $Ar^2$ and $Ar^3$, which may be the same or different, each represents an aryl group or a heterocyclic group, and they have the same meaning as the aryl group and the heterocyclic group represented by $R^1$, $R^2$ and $R^3$ in formula (I) and the preferred ranges are also the same $Ar^1$, $R^4$, $R^5$, $R^6$, $X^1$ and Y have the same meaning as those in formula (III) and the preferred ranges are also the same.

The compound represented by formula (V) will be described below.

In formula (V), $Ar^1$, $Ar^2$, $Ar^3$, $R^4$ and Y have the same meaning as those in formula (IV) and the preferred ranges are also the same. $R^{15}$ and $R^{16}$ each represents a hydrogen atom or a substituent, and the substituents described in $R^1$, $R^2$ and $R^3$ can be applied thereto, provided that $R^{15}$ and $R^{16}$ are not linked to each other. $X^2$ represents an oxygen atom, a sulfur atom, N—$R^{X4}$ or $CR^{X5}R^{X6}$. $R^{X4}$ represents a hydrogen atom, an aliphatic hydrocarbon group, an aryl group or a heterocyclic group. $R^{X5}$ and $R^{X6}$, which may be the same or different, each represents a hydrogen atom, an alkyl group, an aryl group, a heterocyclic group, a cyano group, an oxycarbonyl group, a carbamoyl group, a sulfonyl group, a sulfamoyl group, or an acyl group, provided that $R^{X5}$ and $R^{X6}$ do not represent hydrogen atoms at the same time, and $R^{X5}$ and $R^{X6}$ may be linked to each other to form a ring.

$R^{X4}$, $R^{X5}$ and $R^{X6}$ have the same meaning as $R^{X1}$, $R^{X2}$ and $R^{X3}$ described above.

$R^{15}$ and $R^{16}$ each preferably represents an alkyl group or an aryl group.

The compound represented by formula (VI) will be described below.

In formula (VI), $Ar^1$, $Ar^2$, $Ar^3$, $R^4$, $X^2$ and Y have the same meaning as those in formula (V) and the preferred ranges are also the same, provided that when $X^2$ represents an oxygen atom and $Ar^1$ represents a phenyl group, at least one of $Ar^2$ and $Ar^3$ represents a substituted phenyl group, a naphthyl group, an anthryl group, a phenanthryl group, a pyrenyl group, an indenyl group, a perylenyl group or a heterocyclic group. The examples of the substituent in the substituted phenyl group include an alkyl group, a polymer chain, an alkenyl group, an aryl group, an alkoxy group and a substituted amino group.

$R^7$, $R^8$, $R^9$ and $R^{10}$ have the same meaning as $R^5$ and $R^6$ in formula (IV), and preferably all of them represent hydrogen atoms.

The compounds represented by formulae (I), (III) to (VI) may be low molecular weight compounds, may be high molecular weight compounds having the residual monomers of the compounds represented by formulae (I), (III) to (VI) bonded to the polymer main chains (preferably having a weight average molecular weight of from 1,000 to 5,000,000, more preferably from 5,000 to 2,000,000, and particularly preferably from 10,000 to 1,000,000), or may be high molecular weight compounds having the skeletons of the compounds represented by formulae (I), (III) to (VI) at the main chains (preferably having a weight average molecular weight of from 1,000 to 5,000,000, more preferably from 5,000 to 2,000,000, and particularly preferably from 10,000 to 1,000,000). The high molecular weight compounds may be homopolymers or copolymers with other monomers.

The compounds represented by formulae (I), (III) to (VI) are preferably low molecular weight compounds. Further, formulae (I) to (VI) take limiting structures for convenience sake but the compounds may be tautomers thereof.

With respect to the compound represented by formula (I), preferred combinations will be described. $R^1$, $R^2$ and $R^3$, which may be the same or different, each represents a monocyclic or bicyclic aryl group having from 6 to 30 carbon atoms, a 5- or 6-membered aromatic heterocyclic group containing a nitrogen atom, an oxygen atom or a sulfur atom and having from 1 to 20 carbon atoms, or an alkyl group having from 1 to 20 carbon atoms. At least one of $R^1$, $R^2$ and $R^3$ represents the above-described aryl group or heterocyclic group, and contains the group represented by formula (II) as a substituent. $R^1$, $R^2$ and $R^3$ each may have a substituent, and examples of the substituents include an alkyl group, an alkenyl group, an aralkyl group, an aryl group, an alkoxyl group, an amino group, an acyl group, an alkoxycarbonyl group, an aryloxycarbonyl group, a carbonylamino group, a sulfonylamino group, a sulfamoyl group, a carbamoyl group, a hydroxyl group, and a heterocyclic group, and these groups may further be substituted.

In formula (II), $R^4$, $R^5$ and $R^6$ each represents a hydrogen atom or a substituent, and examples of the substituents include an alkyl group having from 1 to 20 carbon atoms, an alkoxyl group having from 1 to 20 carbon atoms, an alkylthio group having from 1 to 20 carbon atoms, an alkenyl group having from 2 to 20 carbon atoms, an acyl group having from 2 to 20 carbon atoms, an alkoxycarbonyl group having from 2 to 20 carbon atoms, a substituted or unsubstituted amino group having from 0 to 20 carbon atoms, a substituted sulfonyl group having from 0 to 20 carbon atoms, and a cyano group. $R^5$ and $R^6$ may be linked to each other to form a ring, and the ring formed by linking $R^5$ and $R^6$ preferably represents an aromatic carbocyclic ring or an aromatic heterocyclic ring. $X^1$ represents an oxygen atom, a sulfur atom, $N-R^{X1}$ or $CR^{X2}R^{X3}$, $R^{X1}$ preferably represents a hydrogen atom, an alkyl group, an aryl group or a heterocyclic group, and $R^{X2}$ and $R^{X3}$ each preferably represents a hydrogen atom, an alkyl group, an aryl group, an heterocyclic group, a cyano group, an oxycarbonyl group, a carbamoyl group, a sulfonyl group, a sulfamoyl group or an acyl group. $R^{X2}$ and $R^{X3}$ do not represent hydrogen atoms at the same time $R^{X2}$ and $R^{X3}$ may be linked to each other to form a ring.

Y represents an oxygen atom, a sulfur atom, or $N-R^{Y1}$, and $R^{Y1}$ represents a hydrogen atom or a substituent. $R^{Y1}$ has the same meaning as $R^{X1}$.

The more preferred combination in the compound represented by formula (I) is represented by formula (III).

In formula (III), $Ar^1$ represents a divalent monocyclic or bicyclic aryl group having from 6 to 20 carbon atoms, or a divalent 5- or 6-membered aromatic heterocyclic group containing a nitrogen atom, an oxygen atom or a sulfur atom and having from 1 to 20 carbon atoms. $X^1$ represents an oxygen atom, a sulfur atom, $N-R^{X1}$ or $CR^{X2}R^{X3}$, and $R^{X1}$ preferably represents a hydrogen atom, an alkyl group, an aryl group or a heterocyclic group, and $R^{X2}$ and $R^{X3}$ each preferably represents a hydrogen atom, an alkyl group, an aryl group, a heterocyclic group, a cyano group, an oxycarbonyl group, a carbamoyl group, a sulfonyl group, a sulfamoyl group or an acyl group. $R^{X2}$ and $R^{X3}$ do not represent hydrogen atoms at the same time. $R^{X2}$ and $R^{X3}$ may be linked to each other to form a ring. The ring formed by linking $R^{X2}$ and $R^{X3}$ is represented by formula (A). $R^1$, $R^2$, $R^4$, $R^5$, $R^6$ and Y have the same meaning as the combinations in formula (I).

The more preferred combination in the compound represented by formula (III) is represented by formula (IV). In formula (IV), $Ar^1$ has the same meaning as in formula (III), $Ar^2$ or $Ar^3$ each represents a phenyl or naphthyl group having from 6 to 20 carbon atoms, or a 5- or 6-membered aromatic heterocyclic group containing a nitrogen atom, an oxygen atom or a sulfur atom and having from 1 to 20 carbon atoms, and still more preferably a 5- or 6-membered aromatic heterocyclic group containing one or two of a nitrogen atom or a sulfur atom. Specific examples of the heterocyclic rings include, e.g., pyrrolidine, piperidine, piperazine, morpholine, thiophene, furan, pyrrole, imidazole, pyrazole, pyridine, pyrazine, pyridazine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phenazine, tetrazole, benzimidazole, benzoxazole, benzothiazole, benzotriazole, and tetraazaindene. $X^1$ represents an oxygen atom, a sulfur atom, $N-R^{X1}$ or $CR^{X2}R^{X3}$, and $R^{X1}$ represents a hydrogen atom, an alkyl group, an aryl group or a heterocyclic group, and $R^{X2}$ and $R^{X3}$ each represents a hydrogen atom, an alkyl group, an aryl group, a heterocyclic group, a cyano group, an oxycarbonyl group, a carbamoyl group, a sulfonyl group, a sulfamoyl group or an acyl group. $R^{X2}$ and $R^{X3}$ do not represent hydrogen atoms at the same time. $R^{X2}$ and $R^{X3}$ may be linked to each other to form a ring. The ring formed by linking $R^{X2}$ and $R^{X3}$ is represented by formula (A).

$R^{X1}$, $R^{X2}$ and $R^{X3}$ each more preferably represents a hydrogen atom, an alkyl group having from 1 to 20 carbon atoms, a monocyclic or bicyclic aryl group having from 6 to 20 carbon atoms, or a 5- or 6-membered aromatic heterocyclic group containing a nitrogen atom, an oxygen atom or a sulfur atom and having from 1 to 20 carbon atoms. The alkyl group represented by $R^{X2}$ and $R^{X3}$ is preferably a perfluoroalkyl group, i.e., a straight chain, branched or cyclic alkyl group having a fluorine atom as a substituent (preferably an alkyl group having from 1 to 30, more preferably from 1 to 20, and particularly preferably from 1 to 12, carbon atoms, e.g., trifluoromethyl, pentafluoromethyl). The oxycarbonyl group, the carbamoyl group, the sulfonyl group, the sulfamoyl group or the acyl group represented by $R^{X2}$ and $R^{X3}$ is an oxycarbonyl group, a carbamoyl group, a sulfonyl group, a sulfamoyl group or an acyl group substituted with an aliphatic hydrocarbon group, an aryl group or a heterocyclic group. The aliphatic hydrocarbon group in this case is a straight chain, branched or cyclic alkyl group (preferably an alkyl group having from 1 to 30, more preferably from 1 to 20, and still more preferably from 1 to 12, carbon atoms, e.g., methyl, ethyl, isopropyl, tert-butyl, n-octyl, n-decyl, n-hexadecyl, cyclopropyl, cyclopentyl, cyclohexyl, trifluoromethyl), an alkenyl group (preferably an alkenyl group having from 2 to 30, more preferably from 2 to 20, and still more preferably from 2 to 12, carbon atoms, e.g., vinyl, allyl, 2-butenyl, 3-pentenyl), or an alkynyl group (preferably an alkynyl group having from 2 to 30, more preferably from 2 to 20, and still more preferably from 2 to 12, carbon atoms, e.g., propargyl, 3-pentynyl), preferably an alkyl group or an alkenyl group, and more preferably a methyl group, an ethyl group, a propyl group, a butyl group, a trifluoromethyl group or an allyl group. The aryl group in this case is preferably a monocyclic or bicyclic aryl group having from 6 to 30 carbon atoms (e.g., phenyl, naphthyl), more preferably a phenyl group having from 6 to 20 carbon atoms, and still more preferably a phenyl group having from 6 to 12 carbon atoms. The heterocyclic group in this case is a 3- to 10-membered saturated or unsaturated heterocyclic ring containing at least one N, O or S atom and having from 1 to 20 carbon atoms, and the heterocyclic ring may be a monocyclic ring or may form a condensed ring with other rings. $R^{X2}$ and $R^{X3}$ do not represent hydrogen atoms at the same time. $R^{X2}$ and $R^{X3}$ may be linked to each other to form a ring. The ring formed by linking $R^{X2}$ and $R^{X3}$ is preferably represented by the following formula (B), (C), (D), (E), (F) or (G).

Y preferably represents an oxygen atom, a sulfur atom, or N—$R^{Y1}$, and $R^{Y1}$ represents an alkyl group having from 1 to 20 carbon atoms.

$R^4$, $R^5$ and $R^6$ have the same meaning as the combinations in formula (I).

The more preferred combinations in the compound represented by formula (IV) are represented by formula (V) or (VI). In formula (V), $Ar^1$, $Ar^2$ and $Ar^3$ have the same meaning as $Ar^1$, $Ar^2$ and $Ar^3$ in formula (IV), $R^4$, $R^{15}$ and $R^{16}$ each represents a hydrogen atom or a substituent, and examples of the substituents include an alkyl group having from 1 to 20 carbon atoms, an alkoxyl group having from 1 to 20 carbon atoms, an alkylthio group having from 1 to 20 carbon atoms, an alkenyl group having from 2 to 20 carbon atoms, an aryl group having from 6 to 20 carbon atoms, an acyl group having from 2 to 20 carbon atoms, an alkoxycarbonyl group having from 2 to 20 carbon atoms, a substituted sulfonyl group having from 1 to 20 carbon atoms, a substituted or unsubstituted amino group having from 0 to 20 carbon atoms, and a cyano group. $R^{15}$ and $R^{16}$ are not linked. $R^{15}$ and $R^{16}$ each particularly preferably represents the above alkyl group or aryl group.

$X^2$ represents an oxygen atom, a sulfur atom, N—$R^{X4}$ or $CR^{X5}R^{X6}$. $R^{X4}$, $R^{X5}$ and $R^{X6}$ each represents a hydrogen atom, an alkyl group having from 1 to 20 carbon atoms, a monocyclic or bicyclic aryl group having from 6 to 20 carbon atoms, or a 5- or 6-membered aromatic heterocyclic group containing a nitrogen atom, an oxygen atom or a sulfur atom and having from 1 to 20 carbon atoms. The alkyl group represented by $R^{X5}$ and $R^{X6}$ is preferably a perfluoroalkyl group, i.e., a straight chain, branched or cyclic alkyl group having a fluorine atom as a substituent (preferably an alkyl group having from 1 to 30, more preferably from 1 to 20, and still more preferably from 1 to 12, carbon atoms, e.g., trifluoromethyl, pentafluoromethyl). The oxycarbonyl group, the carbamoyl group, the sulfonyl group, the sulfamoyl group or the acyl group represented by $R^{X5}$ and $R^{X6}$ is an oxycarbonyl group, a carbamoyl group, a sulfonyl group, a sulfamoyl group or an acyl group substituted with an aliphatic hydrocarbon group, an aryl group or a heterocyclic group. The aliphatic hydrocarbon group in this case is a straight chain, branched or cyclic alkyl group (preferably an alkyl group having from 1 to 30, more preferably from 1 to 20, and still more preferably from 1 to 12, carbon atoms, e.g., methyl, ethyl, isopropyl, tert-butyl, n-octyl, n-decyl, n-hexadecyl, cyclopropyl, cyclopentyl, cyclohexyl, trifluoromethyl), an alkenyl group (preferably an alkenyl group having from 2 to 30, more preferably from 2 to 20, and still more preferably from 2 to 12, carbon atoms, e.g., vinyl, allyl, 2-butenyl, 3-pentenyl), or an alkynyl group (preferably an alkynyl group having from 2 to 30, more preferably from 2 to 20, and still more preferably from 2 to 12, carbon atoms, e.g., propargyl, 3-pentynyl), preferably an alkyl group or an alkenyl group, and more preferably a methyl group, an ethyl group, a propyl group, a butyl group, a trifluoromethyl group or an allyl group. The aryl group in this case is preferably a monocyclic or bicyclic aryl group having from 6 to 30 carbon atoms (e.g., phenyl, naphthyl), more preferably a phenyl group having from 6 to 20 carbon atoms, and still more preferably a phenyl group having from 6 to 12 carbon atoms. The heterocyclic group in this case is a 3- to 10-membered saturated or unsaturated heterocyclic ring containing at least one N, O or S atom, and the heterocyclic ring may be a monocyclic ring or may form a condensed ring with other rings. $R^{X5}$ and $R^{X6}$ do not represent hydrogen atoms at the same time. $R^{X5}$ and $R^{X6}$ maybe linked to each other to form a ring. The ring formed by linking $R^{X5}$ and $R^{X6}$ is represented by formula (B) (C), (D), (E), (F) or (G).

Y particularly preferably represents an oxygen atom or a sulfur atom.

In formula (VI), $Ar^1$, $Ar^2$, $Ar^3$, $R^4$, $X^2$ and Y have the same meaning as those in formula (IV), $R^7$, $R^8$, $R^9$ and $R^{10}$ each represents a hydrogen atom or a substituent, and examples of the substituents include an alkyl group having from 1 to 20 carbon atoms, an alkoxyl group having from 1 to 20 carbon atoms, an alkylthio group having from 1 to 20 carbon atoms, an alkenyl group having from 2 to 20 carbon atoms, an acyl group having from 2 to 20 carbon atoms, an alkoxycarbonyl group having from 2 to 20 carbon atoms, a substituted sulfonyl group having from 0 to 20 carbon atoms, a substituted or unsubstituted amino group having from 0 to 20 carbon atoms, and a cyano group. $R^7$, $R^8$, $R^9$ and $R^{10}$ each particularly preferably represents a hydrogen atom. When $X^2$ and Y both represent oxygen atoms and $Ar^1$ represents a phenyl group, at least one of $Ar^2$ and $Ar^3$ represents a substituted phenyl group (examples of the substituents include an alkyl group, an alkoxyl group, and a substituted or unsubstituted amino group), a naphthyl group or a heterocyclic group.

Specific examples of the compounds represented by formula (I) are shown below but it should not be construed as the present invention is limited thereto.

D-1 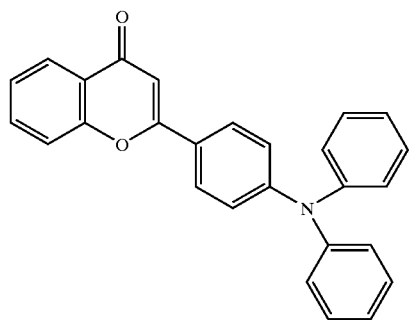
D-2 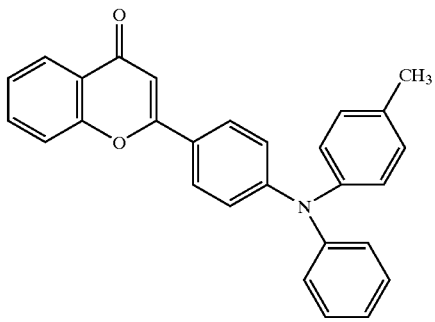
D-3 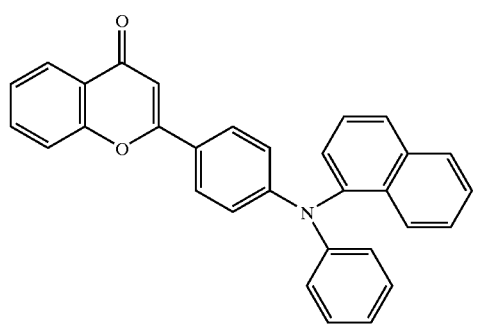
D-4
D-5 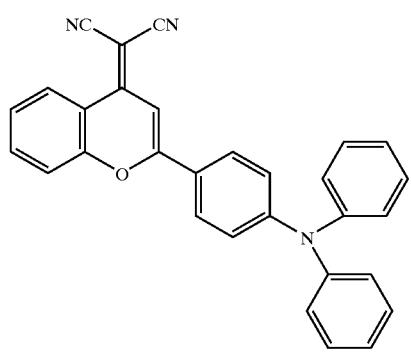
D-6 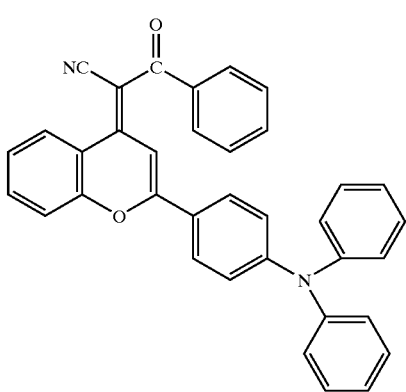
D-7 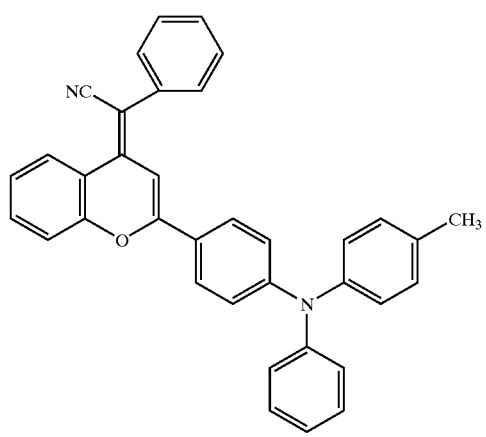
D-8 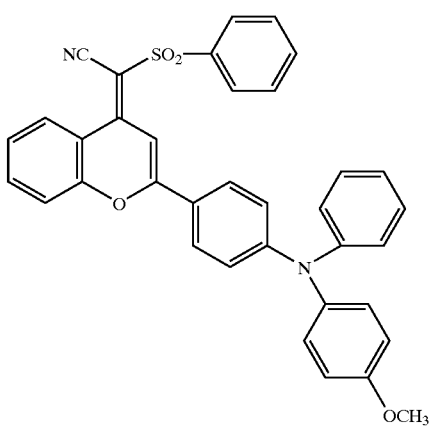

-continued
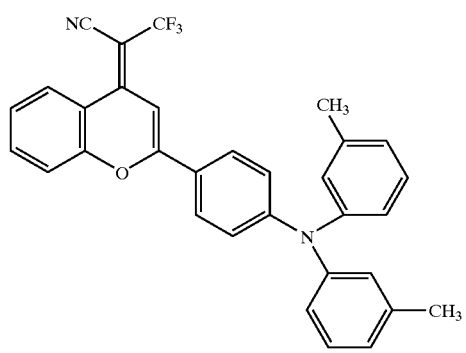
D-9
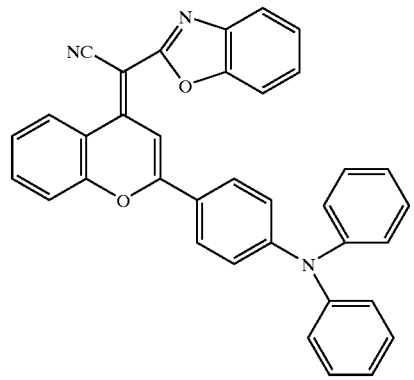
D-10
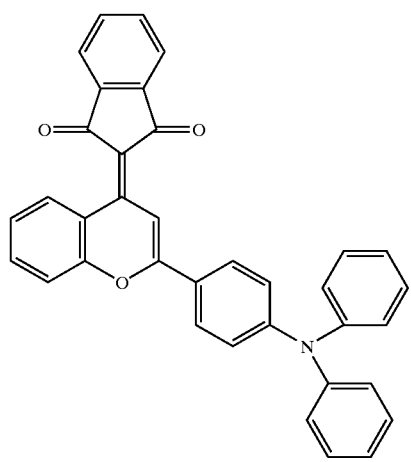
D-11
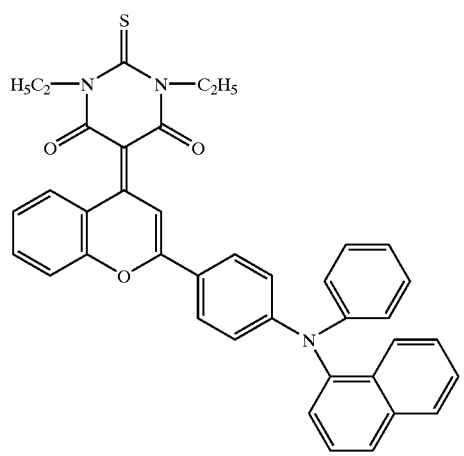
D-12
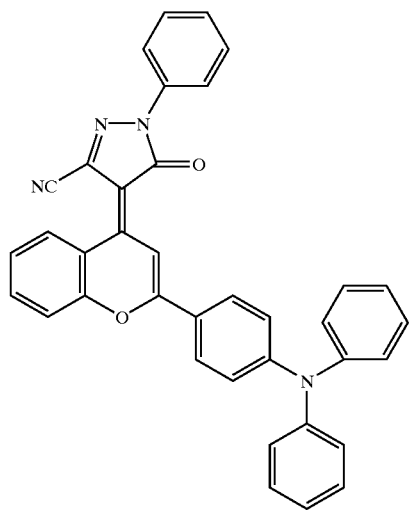
D-13
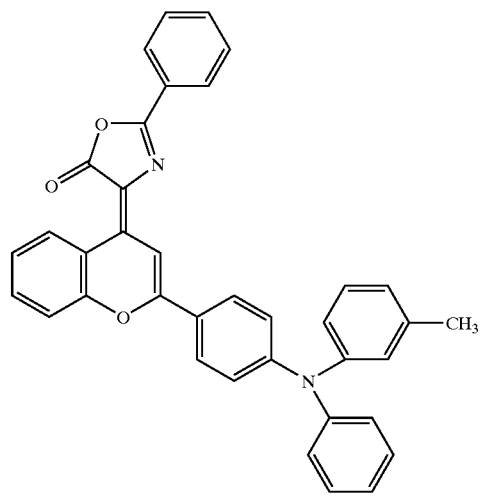
D-14

-continued
D-15
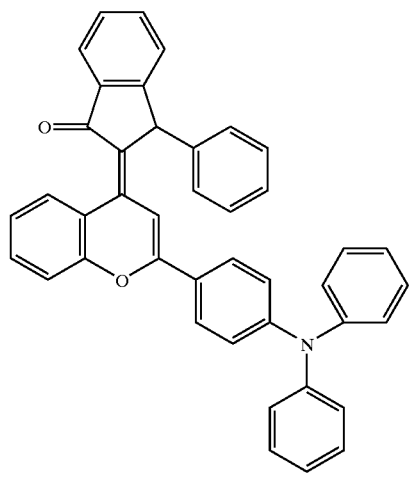
D-16
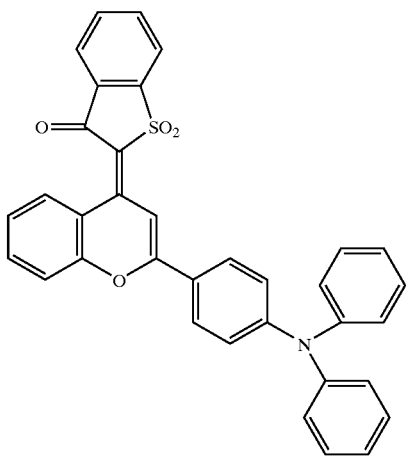
D-17
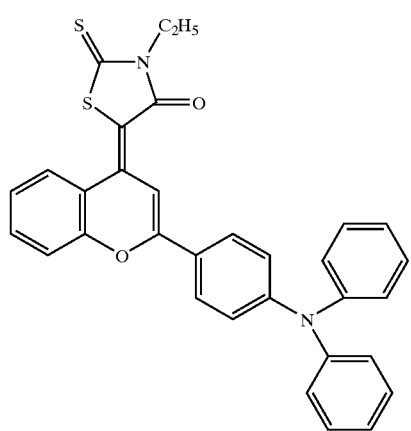
D-18
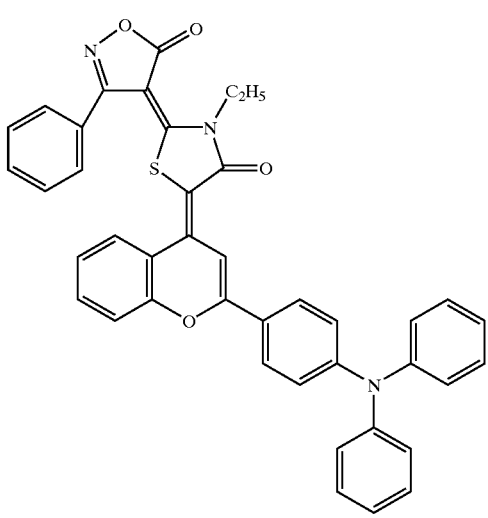
D-19
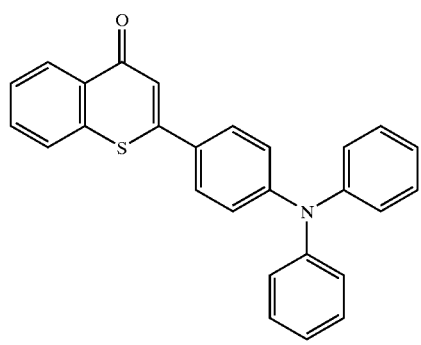
D-20
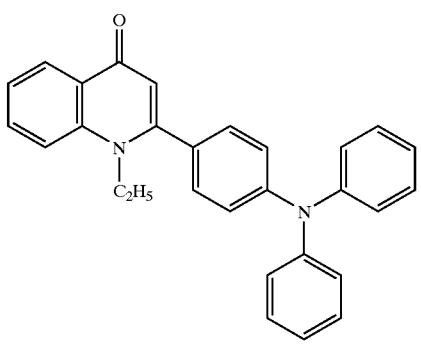
D-21
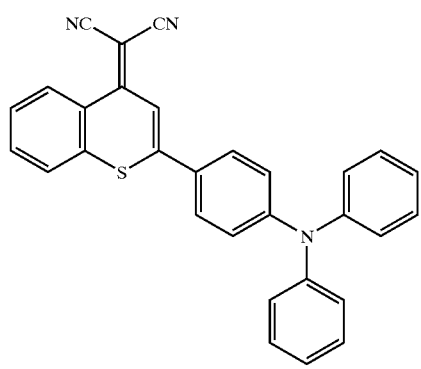
D-22
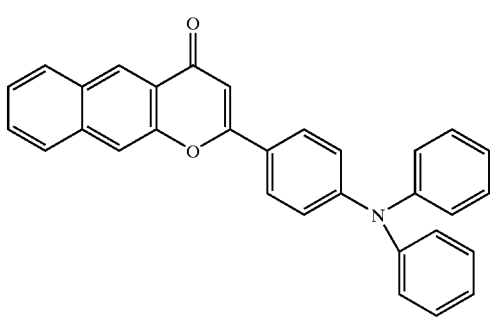

-continued
D-23
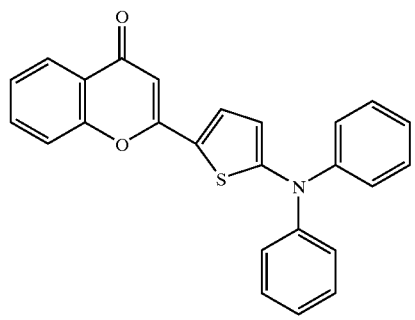
D-24
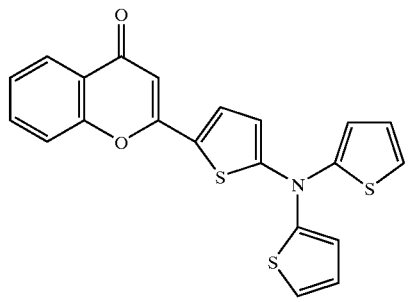
D-25
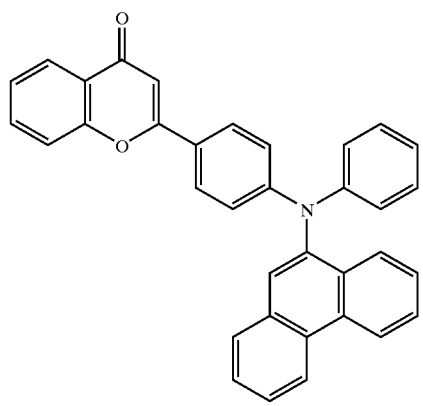
D-26
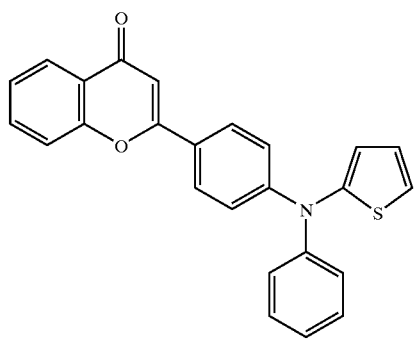
D-27
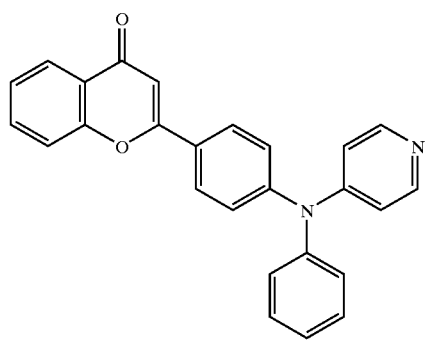
D-28
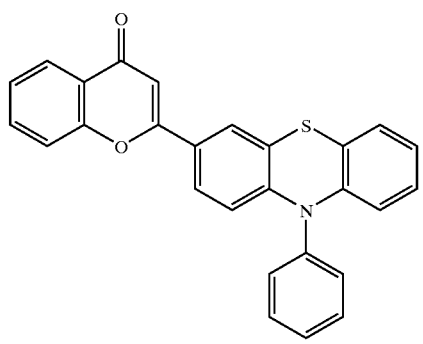
D-29
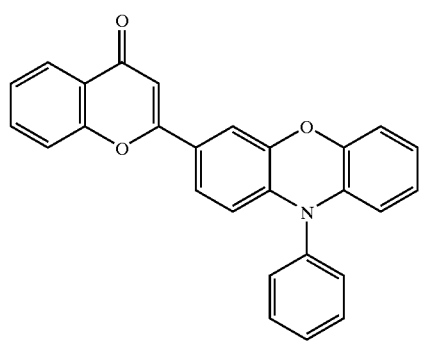
D-30
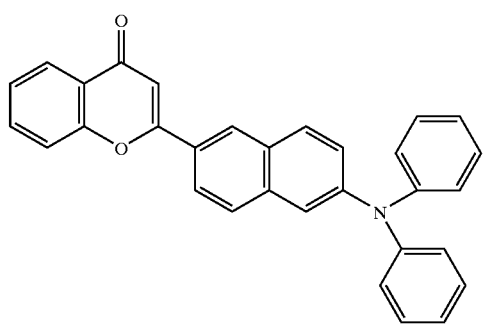

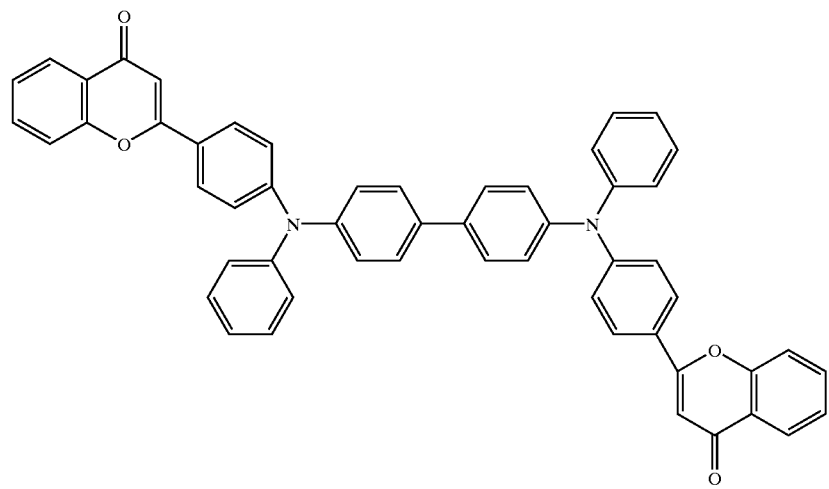
D-31
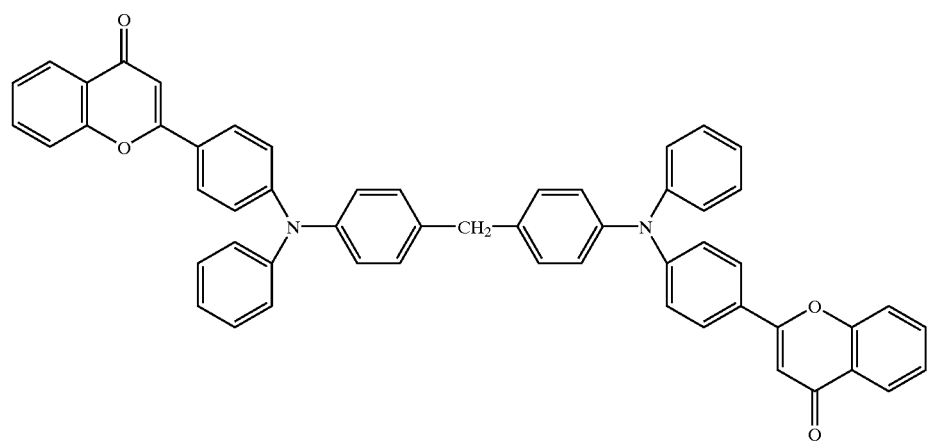
D-32
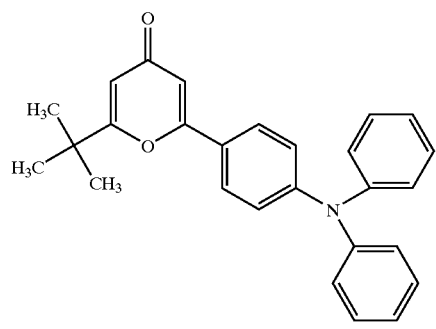
D-33
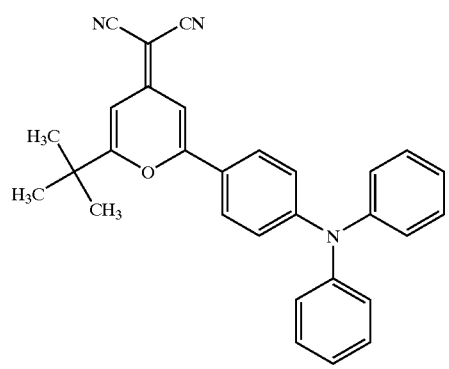
D-34

-continued
D-35
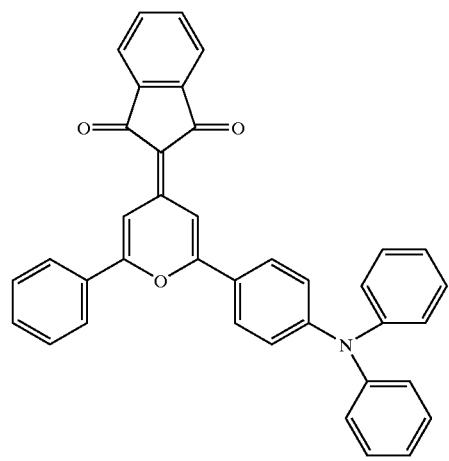
D-36
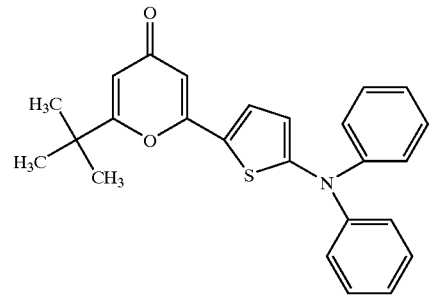
D-37
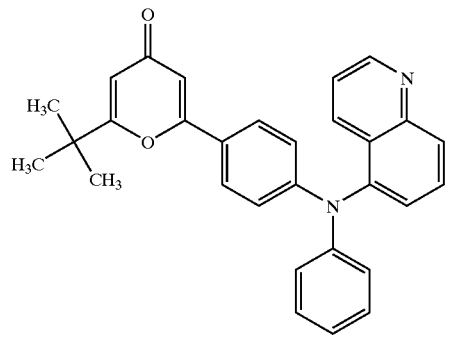
D-38
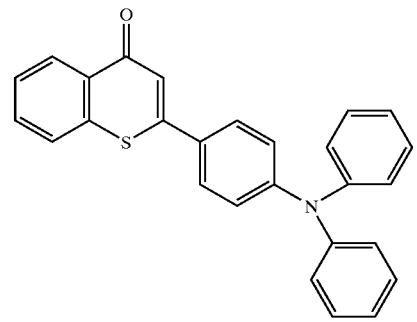
D-39
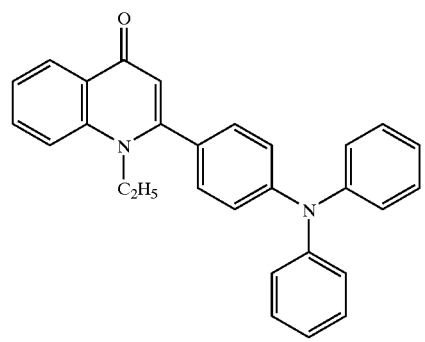
D-40
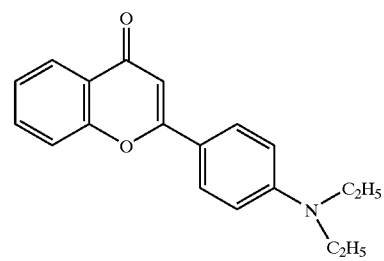
D-41
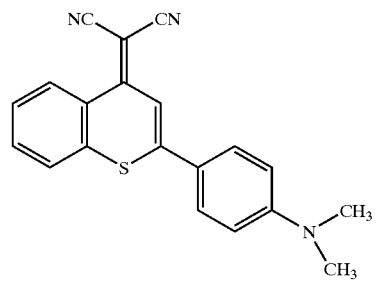
D-42
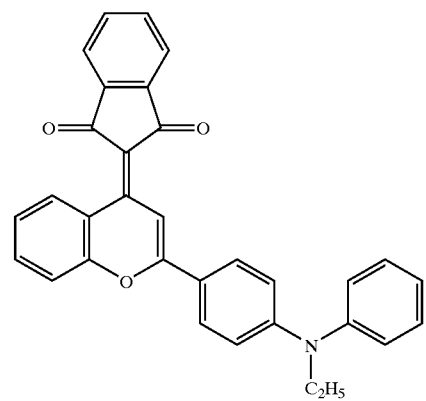

-continued
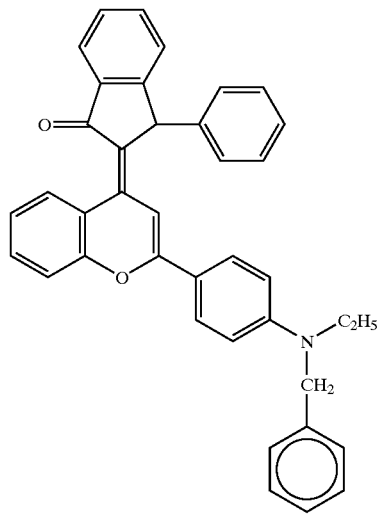
D-43
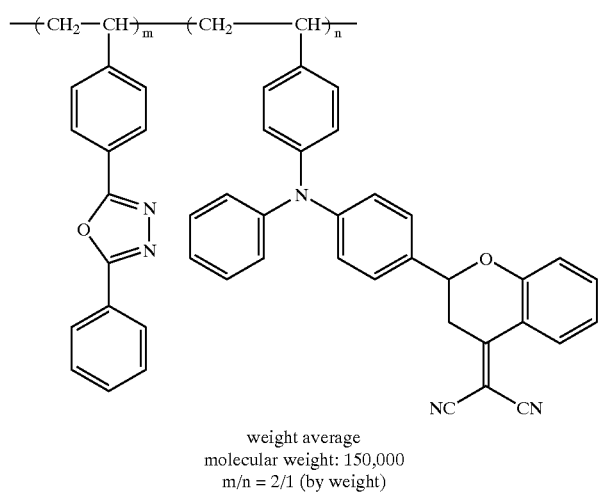
weight average
molecular weight: 150,000
m/n = 2/1 (by weight)
D-44
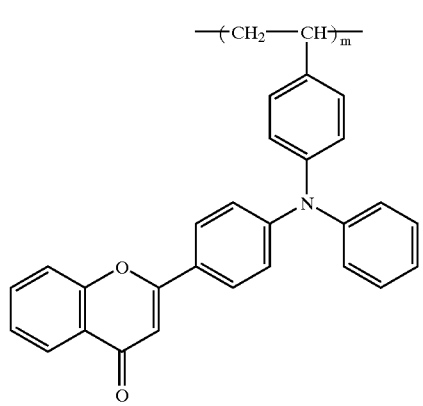
weight average
molecular weight: 35,000
(in terms of polystyrene)
D-45
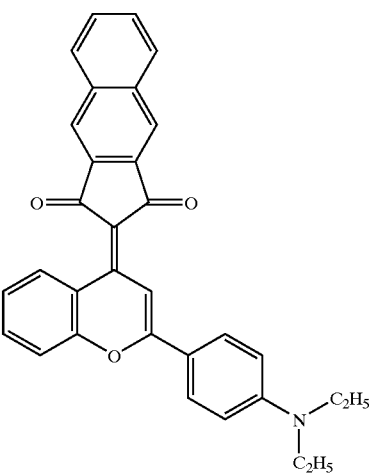
D-46

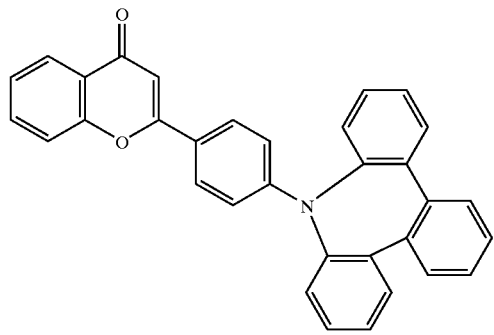

D-47

In the next place, some synthesis examples of the compounds represented by formula (I) will be described below.

The compounds represented by formula (I) can be synthesized by various methods, for example, the following methods of formula (A) and formula (B) can be used, wherein $R^1$, $R^2$, $R^{x2}$ and $R^{x3}$ have the same meaning in formula (I)

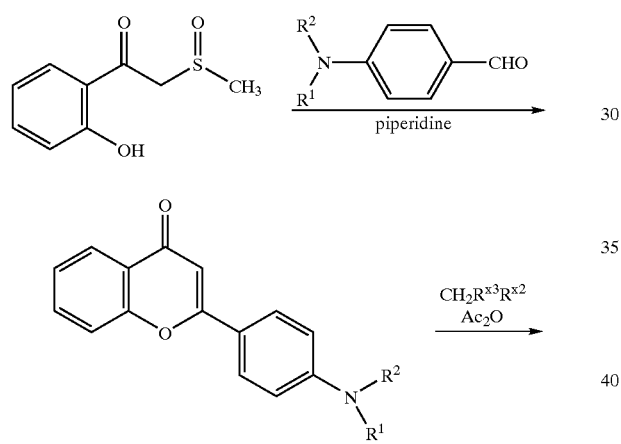

Formula (A)

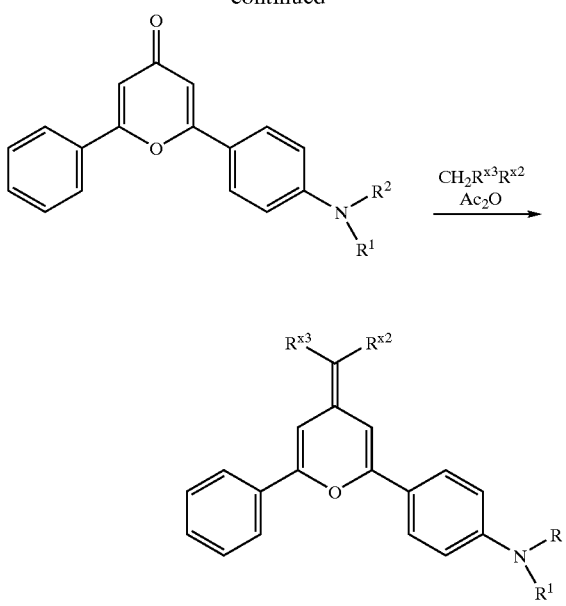

Formula (B)

SYNTHESIS EXAMPLE 1

Synthesis of Eemplified Compound (D-1)

SYNTHESIS EXAMPLE 1
Synthesis of Exemplified Compound (D-1)

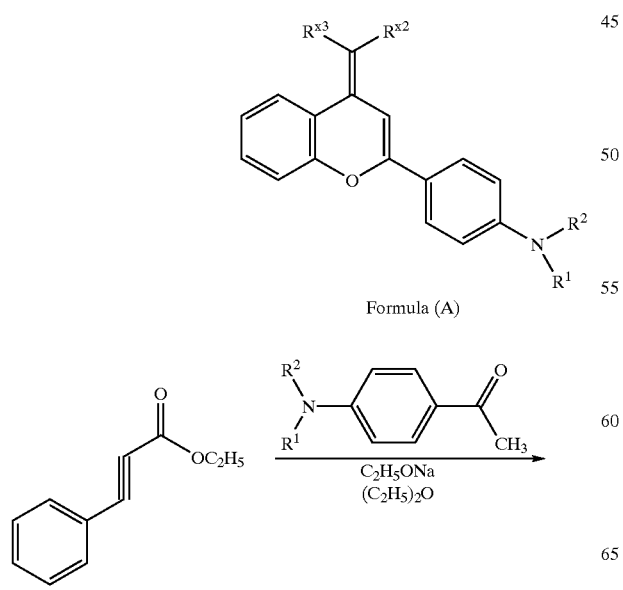

(Compound A)     (Compound B)

-continued

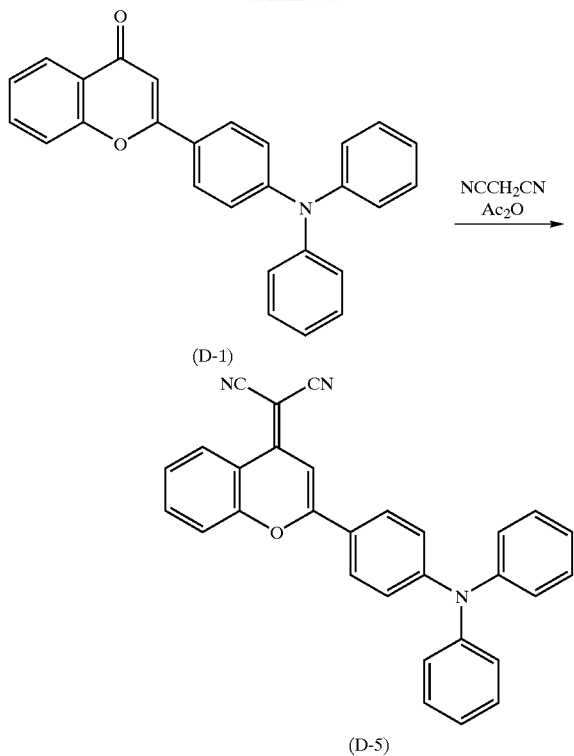

(D-1)

(D-5)

Four point zero (4.0) grams of Compound A and 5.4 g of Compound B were dissolved in 100 ml of toluene, and 1 ml of piperidine was added thereto. The mixture was refluxed with heating for 2 hours. The tar obtained by concentrating the reaction solution was refined by silica gel column chromatography. The thus-obtained crystals were recrystallized with ethanol two times, thereby 4.5 g of exemplified Compound (D-1) was obtained. (mp: 142 to 144° C.).

SYNTHESIS EXAMPLE 2

Synthesis of Exemplified Compound (D-5)

Then, 0.78 g of Compound (D-1) and 0.20 g of malononitrile were dissolved in 5 ml of acetic anhydride, and the solution was stirred with heating for 9 hours. After completion of the reaction, the reaction solution was allowed to be cooled. The solid precipitated was refined by silica gel column chromatography. The thus-obtained crystals were recrystallized with chloroform-ethanol two times, thereby 290 mg of exemplified Compound (D-5) was obtained. (mp: 224 to 227° C.).

SYNTHESIS EXAMPLE 3

Synthesis of Exemplified Compound (D-11)

Zero point seven eight (0.78) grams of Compound (D-1) and 0.44 g of 1,3-indanedione were dissolved in 5 ml of acetic anhydride, and the solution was stirred with heating for 9 hours. After completion of the reaction, the reaction solution was allowed to be cooled. The solid precipitated was refined by silica gel column chromatography. The thus-obtained crystals were recrystallized with chloroform-ethanol two times, thereby 220 mg of exemplified Compound (D-11) was obtained. (mp: 189 to 193° C.)

In the next place, an EL device containing the arylamine compound according to the present invention will be described. The process of forming the organic layer of an EL device containing the arylamine compound according to the present invention is not particularly limited and, e.g., a resistance heating deposition process, an electron beam process, a sputtering process, a molecular laminating process, a coating process, and an ink jet process can be used. A resistance heating deposition process and a coating process are preferably used in view of characteristic aspect and productivity.

The light emitting device according to the present invention comprises a pair of electrodes of the anode and the 0cathode having formed therebetween a luminescent layer or a plurality of thin layers of organic compound including a luminescent layer, and may comprise a positive hole-injecting layer, a positive hole-transporting layer, an electron-injecting layer, an electron-transporting layer, a protecting layer, etc., in addition to a luminescent layer. Each of these layers may have different functions. Various materials can be used to form each layer.

The anode is to supply positive holes to a positive hole-injecting layer, a positive hole-transporting layer, a luminescent layer, etc., and metals, alloys, metallic oxides, electrically conductive compounds, or mixtures of these compounds can be used therefor, and materials having a work function of 4 eV or more are preferably used. Specific examples of the materials of the anode include electrically conductive metallic oxides such as a tin oxide, a zinc oxide, an indium oxide, an indium tin oxide (ITO), etc., metals such as gold, silver, chromium, nickel, etc., mixtures or laminations of these metals with electrically conductive metallic oxides, inorganic electrically conductive materials such as copper iodide, copper sulfide, etc., organic electrically conductive materials such as polyaniline, polythiophene, polypyrrole, etc., and laminations of these materials with ITO. Electrically conductive metallic oxides are preferably used, and ITO is particularly preferably used in view of producibility, high conductivity and transparency. The layer thickness of the anode can be selected arbitrarily according to materials used but is generally preferably from 10 nm to 5 μm, more preferably from 50 nm to 1 μm, and still more preferably from 100 nm to 500 nm.

The anode generally comprises lamination formed on a soda-lime glass, non-alkali glass or transparent resin substrate. When a glass substrate is used, non-alkali glass is preferably used for lessening elution of ions from the glass. Further, when soda-lime glass is used, it is preferred to provide a barrier coat such as silica. The thickness of the substrate is not particularly limited so long as it can sufficiently stand the mechanical strength. When glass is used, the thickness is generally 0.2 mm or more, preferably 0.7 mm or more. Various processes are used in manufacturing the anode according to the materials to be used. In the case of using ITO, for example, films are formed by an electron beam process, a sputtering process, a resistance heating deposition process, a chemical reaction process (a sol-gel process), or the process of coating the dispersion of an indium tin oxide. It is possible to reduce the driving voltage or increase the luminous efficacy of the device by the process such as washing of the anode. In the case of using ITO, for instance, UV-ozone processing and plasma processing are effective.

The cathode is to supply electrons to an electron-injecting layer, an electron-transporting layer, a luminescent layer, etc., and the cathode is selected taking into consideration the adhesion with the layers adjacent to the negative electrode such as an electron-injecting layer, an electron-transporting layer, a luminescent layer, etc., ionization potential and stability. As materials of the cathode, metals, alloys, metallic halides, metallic oxides, electrically conductive compounds, or mixtures of these compounds can be used. Specific examples include alkali metals (e.g., Li, Na, K, etc) or fluorides of them, alkaline earth metals (e.g., Mg, Ca, etc.) or fluorides of them, gold, silver, lead, aluminum, sodium-potassium alloys or mixed metals of them, lithium-aluminum alloys or mixed metals of them, magnesium-silver alloys or mixed metals of them, and rare earth metals such as indium, ytterbium, etc., preferably materials having a work function of 4 eV or less, and more preferably aluminum, lithium-aluminum alloys or mixed metals of them, and magnesium-silver alloys or mixed metals of them. The cathode can take not only the monolayer structures of the above compounds and mixtures thereof but also the laminating structured of the above compounds and mixtures thereof. The layer thickness of the cathode can be selected arbitrarily according to the materials used but is generally preferably from 10 nm to 5 $\mu$m, more preferably from 50 nm to 1 $\mu$m, and still more preferably from 100 nm to 1 $\mu$m. Processes such as an electron beam process, a sputtering process, a resistance heating deposition process, and a coating process are used in the manufacture of the cathode, and a single metal can be vapor deposited or two or more components can be deposited at the same time. Further, a plurality of metals can be deposited at the same time to form an alloy electrode, alternatively a previously prepared alloy can be deposited. It is preferred that the sheet resistance of the anode and the cathode be low, preferably several hundred $\Omega/\square$ or less.

The luminescent layer may be formed of any material so long as, when electric field is impressed, the luminescent layer formed does not prevent positive holes from being injected from the anode, or the positive hole-injecting layer and the positive hole-transporting layer, electrons from being injected from the cathode, or the electron-injecting layer and the electron-transporting layer, and offers the functions of transferring the electric charge injected and recombining the electrons and positive holes to effect emission. Preferably the luminescent layer contains the amine compound according to the present invention but other light emitting materials can also be used, e.g., benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, perylene derivatives, perynone derivatives, oxadiazole derivatives, aldazine derivatives, pyrralidine derivatives, cyclopentadiene derivatives, bisstyrylanthracene derivatives, quinacridone derivatives, pyrrolopyridine derivatives, thiadiazolopyridine derivatives, cyclopentadiene derivatives, styrylamine derivatives, aromatic dimethylidyne compounds, various metal complexes represented by metal complexes of 8-quinolinol derivatives and rare earth metal complexes, and polymer compounds such as polythiophene, polyphenylene, and polyphenylene vinylene are exemplified. The layer thickness of the luminescent layer is not particularly restricted but it is generally preferably from 1 nm to 5 $\mu$m, more preferably from 5 nm to 1 $\mu$m, and still more preferably from 10 nm to 500 nm.

The luminescent layer can be formed by any process, e.g., a resistance heating deposition process, an electron beam process, a sputtering process, a molecular laminating process, a coating process (a spin coating process, a cast coating process, a dip coating process), an LB process or an ink jet process is used, preferably a resistance heating deposition process and a coating process.

Materials of the positive hole-injecting layer and the positive hole-transporting layer are sufficient if they have any of the functions of injecting positive holes from the anode, transporting positive holes, and barriering off the electrons injected from the cathode. Specific examples of the materials include carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidyne-based compounds, porphyrin-based compounds, polysilane-based compounds, poly(N-vinylcarbazole) derivatives, aniline-based copolymers, and electrically conductive high molecular weight oligomers such as tihophene oligomers and polythiophene. The layer thickness of the positive hole-injecting layer and the positive hole-transporting layer is not particularly limited but the thickness is generally preferably from 1 nm to 5 $\mu$m, more preferably from 5 nm to 1 $\mu$m, and still more preferably from 10 nm to 500 nm. The positive hole-injecting layer and the positive hole-transporting layer may be monolayer structures comprising one or two or more of the above materials, or maybe multilayer structures comprising a plurality of layers of the same compositions or different compositions.

The positive hole-injecting layer and the positive hole-transporting layer are formed by a vacuum deposition process, an LB process, an ink jet process, or a process of dissolving or dispersing the above-described positive hole-injecting and transporting agent in a solvent and coating (a spin coating process, a cast coating process, a dip coating process) In the case a coating process, a positive hole-injecting and transporting agent can be dissolved or dispersed with a resin component. Examples of such resin components include polyvinyl chloride, polycarbonate, polystyrene, polymethyl methacrylate, polybutyl methacrylate, polyester, polysulfone, polyphenylene oxide, polybutadiene, poly(N-vinylcarbazole), hydrocarbon resin, ketone resin, phenoxy resin, polyamide, ethyl cellulose, vinyl acetate, ABS resin, polyurethane, melamine resin, unsaturated polyester resin, alkyd resin, epoxy resin, silicone resin, etc.

Materials of the electron-injecting layer and the electron-transporting layer are sufficient if they have any of the functions of injecting electrons from the cathode, transporting electrons, and barriering off the positive holes injected from the anode. Specific examples of the materials include triazole derivatives, oxazole derivatives, oxadiazole derivatives, fluorenone derivatives, anthraquinodimethane derivatives, anthrone derivatives, diphenylquinone derivatives, thiopyran dioxide derivatives, carbidimide derivatives, fluorenylidene methane derivatives, distyrylpyrazine derivatives, tetracarboxylic acid anhydrides of aromatic condensed rings such as naphthalene and perylene, phthalocyanine derivatives, and various metal complexes represented by metal complexes such as metal complexes of 8-quinolinol derivatives and metal complexes having a ligand such as metal phthalocyanine, benzoxazole or benzothiazole. The layer thickness of the electron-injecting layer and the electron-transporting layer is not particularly restricted but the thickness is generally preferably from 1 nm to 5 $\mu$m, more preferably from 5 nm to 1 $\mu$m, and still more preferably from 10 nm to 500 nm. The electron-injecting layer and the electron-transporting layer may be monolayer structures comprising one or two or more of the above materials, or may be multilayer structures comprising a plurality of layers of the same compositions or different compositions.

The electron-injecting layer and the electron-transporting layer are formed by a vacuum deposition process, an LB process, an ink jet process, or a process of dissolving or dispersing the above-described electron-injecting and transporting agent in a solvent and coating (a spin coating process, a cast coating process, a dip coating process). In the case a coating process, an electron-injecting and transporting agent can be dissolved or dispersed with a resin component. As the resin components, those exemplified in the positive hole-injecting and transporting layers can be applied.

Materials of the protective layer are sufficient if they have the function of preventing substances which accelerates the deterioration of the device, such as water and oxygen, from entering the device. Specific examples of the materials include metals, e.g., In, Sn, Pb, Au, Cu, Ag, Al, Ti, Ni, etc., metallic oxides, e.g., MgO, SiO, $SiO_2$, $Al_2O_3$, GeO, NiO, CaO, BaO, $Fe_2O_3$, $Y_2O_3$, $TiO_2$, etc., metallic fluorides, e.g., $MgF_2$, LiF, $AlF_3$, $CaF_2$, etc., polyethylene, polypropylene, polymethyl methacrylate, polyimide, polyurea, polytetrafluoroethylene, polychlorotrifluoroethylene, polydichlorodifluoroethylene, copolymers of chlorotrifluoroethylene and dichlorodifluoroethylene, copolymers obtained by copolymerizing tetrafluoroethylene with monomer mixtures containing at least one comonomer, fluorine-containing copolymers having cyclic structure at the main chain of the copolymer, water-absorbing substances having a water absorption coefficient of 1% or more, and moisture-proof materials having a water absorption coefficient of 0.1% or less.

The forming process of the protective layer is also not particularly restricted and, e.g., a vacuum deposition process, a sputtering process, a reactive sputtering process, an MBE (molecular beam epitaxy) process, a cluster ion beam process, an ion-plating process, a plasma polymerization process (a high frequency exciting ion-plating process), a plasma CVD process, a laser CVD process, a heat CVD process, a gas source CVD process, a coating process, or an ink jet process can be applied.

The present invention will be specifically described below with referring to examples, but it should not be construed as the present invention is limited thereto.

EXAMPLE 1

A transparent supporting substrate comprising a glass substrate of a size of 25 mm×25 mm×0.7 mm having coated thereon ITO in a thickness of 150 nm (manufactured by Tokyo Sanyo Shinku Co., Ltd.) was used. After this transparent supporting substrate was subjected to etching and washing, TPD (N,N'-bis(3-methylphenyl)-N,N'-diphenylbenzidine) in a thickness of about 40 nm, the compound shown in Table 1 below in a thickness of about 40 nm, and Alq (tris(8-hydroxyquinolinato)aluminum) in a thickness of about 20 nm were vapor deposited in order in vacuo of $10^{-3}$ to $10^{-4}$ Pa under the substrate temperature condition of room temperature. A mask which had been subjected to patterning (a mask having a luminescent area of 5 mm×5 mm) was set up on the organic thin layer, and magnesium/silver in the ratio of 10/1 was co-deposited in a thickness of 50 nm in a vapor depositing apparatus, then silver was deposited in a thickness of 300 nm, thereby a light emitting device was prepared.

Direct current constant voltage was impressed to the light emitting device to effect emission using source measuring unit model 2400 (manufactured by Toyo Technica Co., Ltd.). The luminance was measured using luminescence meter BM-8 (manufactured by Topcon Co., Ltd.), and the luminescent wavelength was measured using spectrum analyzer PMA-11 (manufactured by Hamamatsu Photonics Co., Ltd.). The results obtained are shown in Table 1 below.

TABLE 1

| Device No. | Compound | Maximum Luminance ($cd/m^2$) | Driving Voltage (V) | Luminescent Wavelength El max (nm) | CIE Chromaticity Coordinates (x, y) | Generation of Dark Spots (after 100 hr. emission) |
|---|---|---|---|---|---|---|
| 101 | Comparative Compound A | 300 | 12 | 469 | (0.17, 0.20) | x |
| 102 | Comparative Compound B | 200 | 11 | 485 | (0.17, 0.32) | x |
| 103 | Comparative Compound C (D-1) | 6,400 | 11 | 517 | (0.28, 0.51) | Δ |
| 104 | Exemplified Compound D-2 | 8,700 | 12 | 521 | (0.30, 0.52) | ○ |
| 105 | Exemplified Compound D-3 | 7,600 | 12 | 519 | (0.28, 0.51) | ○ |
| 106 | Exemplified Compound D-5 | 4,200 | 11 | 595 | (0.53, 0.44) | ○ |
| 107 | Exemplified Compound D-11 | 1,600 | 11 | 640 | (0.63, 0.33) | ○ |

○: Dark spots were not observed visually.
Δ: Dark spots were observed a little.
x: Dark spots were observed very much.

TABLE 1-continued

| Device No. | Compound | Maximum Luminance (cd/m$^2$) | Driving Voltage (V) | Luminescent Wavelength El max (nm) | CIE Chromaticity Coordinates (x, y) | Generation of Dark Spots (after 100 hr. emission) |
|---|---|---|---|---|---|---|

Comparative Compound A

Comparative Compound B

As is apparent from the results in Table 1, with the device in which the compound not containing an amino group such as Comparative Compound A or Comparative Compound B is used, luminance is low, dark spots are generated very much and durability is inferior. On the other hand, the compound according to the present invention (Compound D-2, D-3, D-5 or D-11) is capable of high luminance emission when used alone as a luminescent layer, which confirms that the compound according to the present invention can be used as a light emitting material having high durability Above all, Compounds D-2 and D-3, which are the compounds represented by formula (VI), are capable of high luminance emission, and excellent in durability as the generation of dark spots is little after long term emission. Further, Compounds D-5 and D-11 which are the compounds represented by formula (VI), wherein X$^2$ represents CR$^{X5}$R$^{X6}$, are excellent in color purity of a red color. In contrast, dark spots were observed in Comparative Compound C (D-1).

EXAMPLE 2

After ITO substrate was subjected to etching and washing in the same manner as in Example 1, TPD was deposited in a thickness of about 40 nm, and then the compound shown in Table 2 below and Alq (tris(8-hydroxyquinolinato) aluminum) were co-deposited at depositing rate of 0.04 Å/sec and 4 Å/sec, respectively, in a layer thickness of about 40 nm. Further, Alq was deposited alone in a thickness of 20 nm. Subsequently, deposition of the cathode was performed in the same manner as in Example 1 to prepare a light emitting device and evaluation was performed. Furthermore, after being stored at a constant temperature of 85° C. for 2 weeks, each sample was driven at the same current as that right after the preparation of device so as to measure the increase in driving voltage between right after the preparation of device and after storage. The results obtained are shown in Table 2 below.

TABLE 2

| Device No. | Compound | Maximum Luminance (cd/m$^2$) | Driving Voltage (V) | Wavelength El max (nm) | CIE Chromaticity Coordinates (x, y) | Generation of Dark Spots (after 100 hr. emission) | Increase in Driving Voltage after Storage ΔV (V) |
|---|---|---|---|---|---|---|---|
| 201 | Comparative Compound C (D-1) | 6,500 | 13 | 510 | (0.25, 0.48) | ○ | 2.0 |
| 202 | Exemplified Compound D-2 | 5,600 | 13 | 515 | (0.28, 0.51) | ○ | 1.0 |
| 203 | Exemplified Compound D-5 | 5,400 | 13 | 595 | (0.53, 0.44) | ○ | 1.2 |
| 204 | Exemplified Compound D-11 | 3,300 | 13 | 630 | (0.61, 0.36) | ○ | 0.7 |
| 205 | Exemplified Compound D-3 | 6,100 | 13 | 505 | (0.26, 0.48) | ○ | 0.5 |

TABLE 2-continued

| Device No. | Compound | Maximum Luminance (cd/m$^2$) | Driving Voltage (V) | Wavelength El max (nm) | CIE Chromaticity Coordinates (x, y) | Generation of Dark Spots (after 100 hr. emission) | Increase in Driving Voltage after Storage ΔV (V) |
|---|---|---|---|---|---|---|---|
| 206 | Exemplified Compound D-25 | 6,010 | 13 | 510 | (0.25, 0.47) | ○ | 0.4 |

The results in Table 2 show that when the compound according to the present invention is used as a light emitting material for doping, a light emitting device exhibiting high luminance emission and high durability can be obtained. It is understood that the compound in which both of $X^2$ and Y in formula (VI) are oxygen atoms and the phenyl group of the triaryl amine moiety has a substituent or a condensed ring (i.e., D-2, D-3 or D-25) is extremely excellent in storage stability compared to Comparative Compound C in which the triaryl amine moiety does not have a substituent.

EXAMPLE 3

After ITO substrate was subjected to etching and washing in the same manner as in Example 1, 40 mg of poly(N-vinylcarbazole), 12 mg of PBD (2-(4-biphenylyl)-5-(4-tert-butylphenyl)-1,3,4-oxadiazole), and 0.5 mg of the compound described in Table 1 were dissolved in 3 ml of 1,2-dichloroethane and the solution was spin-coated on the above-washed ITO substrate. The film thickness of the thus-formed organic thin layer was about 100 nm. Subsequently, deposition of the cathode was performed in the same manner as in Example 1 to prepare a light emitting device and evaluation was performed. The results obtained are shown in Table 3 below.

TABLE 3

| Device No. | Compound | Maximum Luminance (cd/m$^2$) | Driving Voltage (V) | Luminescent Wavelength El max (nm) |
|---|---|---|---|---|
| 301 | Comparative Compound A | 180 | 15 | 470 |
| 302 | Comparative Compound B | 120 | 15 | 490 |
| 303 | Comparative Compound C (D-1) | 2,400 | 14 | 520 |
| 304 | Exemplified Compound D-2 | 1,800 | 15 | 525 |
| 305 | Exemplified Compound D-5 | 1,200 | 15 | 590 |
| 306 | Exemplified Compound D-11 | 1,000 | 15 | 630 |

It can be apparently seen from the results in Table 3 that, as compared with the comparative samples using Comparative Compounds A and B, the device in which the compound of the present invention is used is capable of high luminance emission with low driving voltage even in a coating process, where emission luminance is generally low.

EXAMPLE 4

After ITO substrate was subjected to etching and washing in the same manner as in Example 1, Alq was deposited in a thickness of about 40 nm. Subsequently, deposition of the cathode was performed in the same manner as in Example 1 to prepare a light emitting device and evaluation was carried out. Luminance at driving voltage 15 V was 450 cd/m$^2$. Red emission with high color purity of λmax=635 nm, and CIE chromaticity coordinates (x, y)=(0.64, 0.33) was observed. It was confirmed that the compound according to the present invention was effective as a combination positive hole-injecting/transporting agent and luminescent agent.

EXAMPLE 5

On an ITO glass substrate subjected to etching and washing in the same manner as in Example 1 were deposited NPD (N,N'-bis (1-naphthyl)-N,N'-diphenylbenzidine) in a thickness of about 40 nm, exemplified Compound D-2 in a thickness of about 20 nm, Bathocuproine in a thickness of about 10 nm, and Alq (tris(8-hydroxyquinolinato) aluminum) in a thickness of about 30 nm. Subsequently, deposition of the cathode was performed in the same manner as in Example 1 to prepare a light emitting device and evaluation was performed. The device showed high luminance emission of 9,600 cd/m$^2$ at driving voltage of 14 V.

EXAMPLE 6

The solution obtained by dissolving 40 mg of poly(N-vinylcarbazole), 12 mg of 2,5-bis(1-naphthyl)-1,3,4-oxadiazole, 10 mg of tetraphenylbutadiene, 0.5 mg of DCM and 0.1 mg of exemplified Compound D-2 in 3 ml of 1,2-dichloroethane was spin-coated on an ITO glass substrate which had been subjected to etching and washing in the same manner as in Example 1. The thickness of the thus-formed organic layer was about 120 nm. Subsequently, deposition of the cathode was performed in the same manner as in Example 1 to prepare a light emitting device. Direct current voltage was impressed to this device with the ITO electrode as the anode and the Mg/Ag electrode as the cathode and luminous characteristics were examined. White light emitting (luminance: 1,800 cd/m$^2$) on CIE chromaticity coordinates (x, y) of (0.34, 0.34) at driving voltage of 15 V was obtained, which confirmed that the compound according to the present invention was effective for white light emitting.

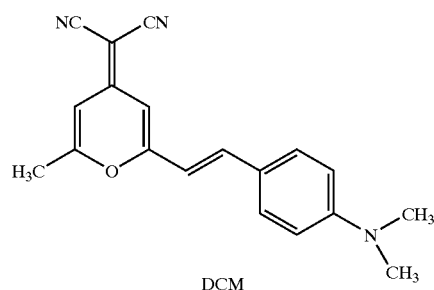

DCM

EFFECT OF THE INVENTION

The organic EL device containing the arylamine compound according to the present invention is capable of high luminance emission. In particular, the non-doping type EL device (a device comprising a luminescent layer of monolayer structure), where high luminance has been thought to be difficult, has realized high luminance emission and high durability Therefore, the manufacture of the device showing less unevenness in performance among devices and advantageous in the production cost as compared with a doping type device has been realized according to the present invention. Further, good luminescent characteristics can be obtained even in a coating system where emission luminance is in general low.

While the invention has been described in detail and with reference to specific examples thereof, it will be apparent to one skilled in the art that various changes and modifications can be made therein without departing from the spirit and scope thereof.

What is claimed is:

1. An amine compound represented by the following formula (V):

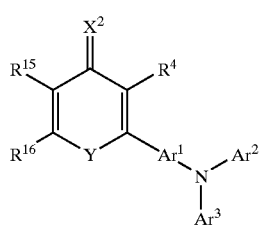

wherein $Ar^1$ represents a divalent aryl or heterocyclic group; $Ar^2$ and $Ar^2$, which are the same or different, each represents an aryl group or a heterocyclic group, $Ar^1$, $A^2$ and $Ar^3$ may be linked to each other to form a ring; $R^4$, $R^{15}$ and $R^{16}$, which are the same or different, each represents an alkyl group having 1 to 20 carbon atoms, an alkoxyl group having from 1 to 20 carbon atoms, an alkylthio group having 1 to 20 carbon atoms, an alkenyl group having from 2 to 20 carbon atoms, an aryl group having from 6 to 20 carbon atoms, an acyl group having from 2 to 20 carbon atoms, an alkoxycarbonyl group having from 2 to 20 carbon atoms, a substituted sulfonyl group having from 1 to 20 carbon atoms, or a cyano group; $X^2$ represents an oxygen atom, a sulfur atom, N—$R^{X4}$ or $CR^{X5}R^{X6}$; $R^{X4}$ represents a hydrogen atom, an aliphatic hydrocarbon group, an aryl group or a heterocyclic group; $R^{X5}$ and $R^{X6}$, which are the same or different, each represents a hydrogen atom, an alkyl group, an aryl group, a heterocyclic group, a cyano group, an oxycarbonyl group, a carbamoyl group, a sulfonyl group, a sulfamoyl group, or an acyl group, provided that $R^{X5}$ and $R^{X6}$ do not represent a hydrogen atom at the same time, $R^{X5}$ and $R^{X6}$ may be linked to each other to form a ring; $R^4$, $R^{15}$, $R^{16}$ and $X^2$ may be linked to each other to form a ring, provided that $R^{15}$ and $R^{16}$ are not linked; Y represents an oxygen atom, a sulfur atom, or N—$R^{Y1}$; and $R^{Y1}$ represents a hydrogen atom or a substituent.

2. A light emitting device comprising a pair of electrodes and at least one organic thin layer between the electrodes, wherein the organic thin layer contains at least one compound represented by the following formula (V):

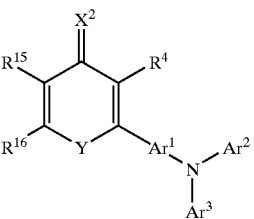

wherein $Ar^1$ represents a divalent aryl or heterocyclic group; $Ar^2$ and $Ar^3$, which are the same or different, each represents an aryl group or a heterocyclic group, $Ar^1$,$Ar^2$ and $Ar^3$ may be linked to each other to form a ring; $R^4$, $R^{15}$ and $R^{16}$, which are the same or different, each represents an alkyl group having 1 to 20 carbon atoms, an alkoxyl group having from 1 to 20 carbon atoms, an alkylthio group having 1 to 20 carbon atoms, an alkenyl group having from 2 to 20 carbon atoms, an aryl group having from 6 to 20 carbon atoms, an acyl group having from 2 to 20 carbon atoms, an alkoxycarbonyl group having from 2 to 20 carbon atoms, a substituted sulfonyl group having from 1 to 20 carbon atoms, or a cyano group: $X^2$ represents an oxygen atom, a sulfur atom, N—$R^{X4}$ or $CR^{X5}R^{X6}$; $R^{X4}$ represents a hydrogen atom, an aliphatic hydrocarbon group, an aryl group or a heterocyclic group; $R^{X5}$ and $R^{X6}$, which are the same or different, each represents a hydrogen atom, an alkyl group, an aryl group, a heterocyclic group, a cyano group, an oxycarbonyl group, a carbamoyl group, a sulfonyl group, a sulfamoyl group, or an acyl group, provided that $R^{X5}$ and $R^{X6}$ do not represent a hydrogen atom at the same time, $R^{X5}$ and $R^{X6}$ may be linked to each other to form a ring; $R^4$, $R^{15}$, $R^{16}$ and $X^2$ may be linked to each other to form a ring, provided that $R^{15}$ and $R^{16}$ are not linked; Y represents an oxygen atom, a sulfur atom, or N—$R^{Y1}$; and $R^{Y1}$ represents a hydrogen atom or a substituent.

3. A light emitting device comprising a pair of electrodes and at least one organic thin layer between the electrodes, wherein at least one layer is a layer containing at least one compound represented by formula (V) as claimed in claim 1 dispersed in a polymer.

4. The amine compound of claim 1, wherein $X^2$ represents a sulfur atom, N—$R^{X4}$ or $CR^{X5}R^{X6}$ and Y represents an oxygen atom, a sulfur atom or N—$R^{Y1}$.

5. The amine compound of claim 1, wherein $X^2$ represents an oxygen atom, a sulfur atom, N—$R^{X4}$ or $CR^{X5}R^{X6}$ and Y represents a sulfur atom or N—$R^{Y1}$.

6. The amine compound of claim 1, wherein $Ar^1$ represents a divalent monocyclic or bicyclic aryl group.

7. The amine compound of claim 1, wherein $Ar^1$ represents a substituted or unsubstituted 5- or 6-membered aromatic heterocyclic group containing a nitrogen atom, an oxygen atom or a sulfur atom.

8. The amine compound of claim 1, wherein $Ar^2$ and $Ar^3$ each represents a phenyl or naphthyl group having from 6 to 20 carbon atoms, or a substituted or unsubstituted 5- or 6-membered aromatic heterocyclic group containing a nitrogen atom, an oxygen atom or a sulfur atom.

9. The amine compound of claim 1, wherein $R^{15}$ and $R^{16}$ each represents an alkyl group having from 1 to 20 carbon atoms.

10. The amine compound of claim 1, wherein $R^{15}$ and $R^{16}$ each represents an aryl group having from 6 to 20 carbon atoms.

11. The light emitting device of claim 2, wherein $X^2$ represents a sulfur atom, N—$Rx^4$ or $CR^{X5}R^{X6}$ and Y represents an oxygen atom, a sulfur atom or N—$R^{Y1}$.

12. The light emitting device of claim 2, wherein $X^2$ represents an oxygen atom, a sulfur atom, N—$R^{X4}$ or $CR^{X5}R^{X6}$ and Y represents a sulfur atom or N—$R^{Y1}$.

13. The light emitting device of claim 2, wherein $Ar^1$ represents a divalent monocyclic or bicyclic aryl group.

14. The light emitting device of claim 2, wherein $Ar^1$ represents a substituted or unsubstituted 5- or 6-membered aromatic heterocyclic group containing a nitrogen atom, an oxygen atom or a sulfur atom.

15. The light emitting device of claim 2, wherein $Ar^2$ and $Ar^3$ each represents a phenyl group or naphthyl group having from 6 to 20 carbon atoms, or a substituted or unsubstituted 5- or 6-membered aromatic heterocyclic group containing a nitrogen atom, an oxygen atom or a sulfur atom.

16. The light emitting device of claim 2, wherein $R^{15}$ and $R^{16}$ each represents an alkyl group having from 1 to 20 carbon atoms.

17. The light emitting device of claim 2, wherein $R^{15}$ and $R^{16}$ each represents an aryl group having from 6 to 20 carbon atoms.

18. An amine compound represented by the following formula (V):

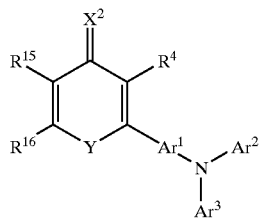

(V)

wherein $Ar^1$ represents a divalent aryl or heterocyclic group; $Ar^2$ and $Ar^3$, which are the same or different, each represents an aryl group or a heterocyclic group, $Ar^1$, $Ar^2$ and $Ar^3$ may be linked to each other to form a ring; $R^4$, $R^{15}$ and $R^{16}$, which are the same or different, each represents a hydrogen atom or a substituent; $X^2$ represents an oxygen atom, a sulfur atom, N—$R^{X4}$ or $CR^{X5}R^{X6}$; $R^{X4}$ represents a hydrogen atom, an aliphatic hydrocarbon group, an aryl group or a heterocyclic group; $R^{X5}$ and $R^{X6}$, which are the same or different, each represents a hydrogen atom, an alkyl group, an aryl group, a heterocyclic group, a cyano group, an oxycarbonyl group, a carbamoyl group, a sulfonyl group, a sulfamoyl group, or an acyl group, provided that $R^{X5}$ and $R^{X6}$ do not represent a hydrogen atom at the same time, $R^{X5}$ and $RX^6$ may be linked to each other to form a ring; $R^4$, $R^{15}$, $R^{16}$ and $X^2$ may be linked to each other to form a ring, provided that $R^{15}$ and $R^{16}$ are not linked; Y represents a sulfur atom or N—$R^{Y1}$; and $R^{Y1}$ represents a hydrogen atom or a substituent.

19. A light emitting device comprising a pair of electrodes and at least one organic thin layer between the electrodes, wherein the organic thin layer contains at least one compound represented by formula (V):

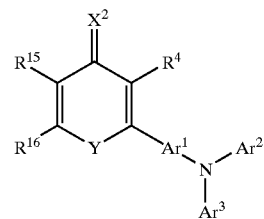

(V)

wherein $Ar^1$ represents a divalent aryl or heterocyclic group; $Ar^2$ and $Ar^3$, which are the same or different, each represents an aryl group or a heterocyclic group, $Ar^1$, $Ar^2$ and $Ar^3$ may be linked to each other to form a ring; $R^4$, $R^{15}$ and $R^{16}$, which are the same or different, each represents a hydrogen atom or a substituent; $X^2$ represents an oxygen atom, a sulfur atom, N—$R^{X4}$ or $CR^{X5}R^{X6}$; $R^{X4}$ represents a hydrogen atom, an aliphatic hydrocarbon group, an aryl group or a heterocyclic group; $R^{X5}$ and $R^{X6}$, which are the same or different, each represents a hydrogen atom, an alkyl group, an aryl group, a heterocyclic group, a cyano group, an oxycarbonyl group, a carbamoyl group, a sulfonyl group, a sulfamoyl group, or an acyl group, provided that $R^{X5}$ and $R^{X6}$ do not represent a hydrogen atom at the same time, $R^{X5}$ and $R^{X6}$ may be linked to each other to form a ring; $R^4$, $R^{15}$, $R^{16}$ and $X^2$ may be linked to each other to form a ring, provided that $R^{15}$ and $R^{16}$ are not linked; Y represents a sulfur atom or N—$R^{Y1}$; and $R^{Y1}$ represents a hydrogen atom or a substituent.

20. An amine compound represented by the following formula (V):

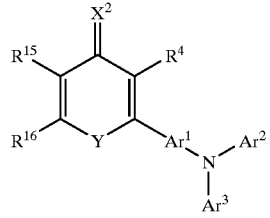

(V)

wherein $Ar^1$ represents a divalent aryl or heterocyclic group; $Ar^2$ and $Ar^3$, which are the same or different, each represents an aryl group or a heterocyclic group, $Ar^1$, $Ar^2$ and $Ar^3$ may be linked to each other to form a ring; $R^4$, $R^{15}$ and $R^{16}$ each represents a hydrogen atom; $X^2$ represents an oxygen atom, a sulfur atom, N—$R^{X4}$ or $CR^{X5}R^{X6}$; $R^{X4}$ represents a hydrogen atom, an aliphatic hydrocarbon group, an aryl group or a heterocyclic group; $R^{X5}$ and $R^{X6}$, which are the same or different, each represents a hydrogen atom, an alkyl group, an aryl group, a heterocyclic group, a cyano group, an oxycarbonyl group, a carbamoyl group, a sulfonyl group, a sulfamoyl group, or an acyl group, provided that $R^{X5}$ and $R^{X6}$ do not represent a hydrogen atom at the same time, $R^{X5}$ and $R^{X6}$ may be linked to each other to form a ring; Y represents an oxygen atom, a sulfur atom, or N—$R^{Y1}$; and $R^{Y1}$ represents a hydrogen atom or a substituent.

21. A light emitting device comprising a pair or electrodes and at least one organic thin layer between the electrodes, wherein the organic thin layer contains at least one compound represented by the following formula (V):

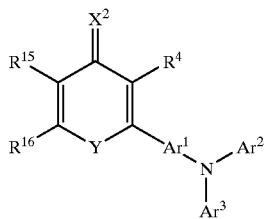

(V)

wherein $Ar^1$ represents a divalent aryl or heterocyclic group; $Ar^2$ and $Ar^3$, which are the same or different, each represents an aryl group or a heterocyclic group, $Ar^1$, $Ar^2$ and $Ar^3$ may be linked to each other to form a ring; $R^4$, $R^{15}$ and $R^{16}$ each represents a hydrogen atom; $X^2$ represents an oxygen atom, a sulfur atom, N—$R^{X4}$ or $CR^{X5}R^{X6}$; $R^{X4}$ represents a hydrogen atom, an aliphatic hydrocarbon group, an aryl group or a heterocyclic group; $R^{X5}$ and $R^{X6}$, which are the same or different, each represents a hydrogen atom, an alkyl group, an aryl group, a heterocyclic group, a cyano group, an oxycarbonyl group, a carbamoyl group, a sulfonyl group, a sulfamoyl group, or an acyl group, provided that $R^{X5}$ and $R^{X6}$ do not represent a hydrogen atom at the same time, $R^{X5}$ and $R^{X6}$ may be linked to each other to form a ring; Y represents an oxygen atom, a sulfur atom, or N—$R^{Y1}$; and $R^{Y1}$ represents a hydrogen atom or a substituent.

* * * * *